(12) United States Patent
Watt et al.

(10) Patent No.: US 6,187,993 B1
(45) Date of Patent: Feb. 13, 2001

(54) TRANSGENIC ANIMALS AS MODEL OF PSORIASIS

(75) Inventors: Fiona M. Watt; Joseph M. Carroll, both of London (GB)

(73) Assignee: Imperial Cancer Research Technology Limited, London (GB)

( * ) Notice: Under 35 U.S.C. 154(b), the term of this patent shall be extended for 0 days.

(21) Appl. No.: 08/894,649

(22) PCT Filed: Feb. 26, 1996

(86) PCT No.: PCT/GB96/00431

§ 371 Date: Nov. 3, 1997

§ 102(e) Date: Nov. 3, 1997

(87) PCT Pub. No.: WO96/27019

PCT Pub. Date: Sep. 6, 1996

(30) Foreign Application Priority Data

Feb. 25, 1995 (GB) .................................................. 9603868
Jul. 15, 1995 (GB) .................................................. 9514535

(51) Int. Cl.⁷ ........................ A01K 67/027; C12N 15/00; C12N 15/85; G01N 33/00
(52) U.S. Cl. ................................. 800/18; 800/3; 800/21; 800/22; 800/25; 435/325
(58) Field of Search ................................... 800/3, 13, 14, 800/18, 21, 22, 25; 435/325

(56) References Cited

FOREIGN PATENT DOCUMENTS

| | | |
|---|---|---|
| WO 90/03983 | 4/1990 | (WO) . |
| WO 92/18147 | 10/1992 | (WO) . |
| WO 93/07885 | 4/1993 | (WO) . |
| WO 93/22430 | 11/1993 | (WO) . |
| WO 93/25071 | 12/1993 | (WO) . |
| WO 94/08603 | 4/1994 | (WO) . |
| WO 94/08605 | 4/1994 | (WO) . |

OTHER PUBLICATIONS

Wall, RJ Transgenic livestock: Progress and prospects for the future. Theriogenology 45: 57–68, 1996.*
Hammer et al. Spontaneous inflammatory disease in transgenic rats expressing HLA–B27 and human b2m: An animal model of HLA–B27–associated human disorders. Cell 63: 1099–1112, Nov. 1990.*
Mullins et al. Fulminant hypertension in transgenic rats harbouring the mouse Ren–2 gene. Nature 344: 541–544, Apr. 1990.*
Mullins et al. Expression of the DBA/2J Ren–2 gene in the adrenal gland of transgenic mice. EMBO J. 8(3): 4065–4072, 1989.*
Taurog et al. HLA–B27 in inbred and non–inbred transgenic mice. J. of Immunol. 141: 4020–4023, Dec. 1988.*
"Chiroscience sets 'gene to drug' target"; SCRIP No. 2240, p. 10 (1997).
Hertle et al, "Integrin expression by human epidermal . . . "; J. Invest. Dermatol., vol. 104(2), pp. 260–265 (1995).

Printout of Medline record for: Bonnekoh et al, J. Invest. Dermatol., 104(1), pp. 58–61 (1995; de Jong et al, Arch. Dermatol. Res., 283(7), pp. 480–482 (1991); and Rasmussen & Celis, J. Invest. Dermatol., 101(4), pp. 560–566 (1993).
"IL–2 fusion toxin promising in psoriasis"; SCRIP 2027, p. 31 (1995).
Pellegrini et al, "Expression, topography and function of integrin receptors are severely . . . "; J. Clin. Invest., vol. 89, pp. 1783–1795 (1992).
Beyaert et al, "Synergistic induction of interleukin–6 by tumour . . . "; J. Immunol., vol. 22, pp. 2181–2184 (1992).
Bata–Csorgo et al, "Kinetics and regulation of human keratinocyte stem cell growth . . . "; J. Clin. Invest., vol. 95, pp. 317–327 (1995).
Nakamura et al, "Keratinocyte–derived Monocyte Chemoattractant Protein 1 . . . "; J. Invest. Dermatol., vol. 105, pp. 635–643 (1995).
Williams et al., "Keratinocyte expression of B7–1 in transgenic mice . . . "; PNAS, vol. 91, pp. 12780–12784 (1994).
Williams & Kupper, "Epidermal expression of intercellular adhesion molecule 1 . . . "; PNAS, vol. 91, pp. 9710–9714 (1994).
HogenEsch et al, "A spontaneous mutation characterised by chronic . . . "; Am. J. Pathol., 143(3), pp. 972–982 (1993).
Sundberg et al, "Full–thickness skin grafts from flaky skin mice to nude . . . "; J. Invest. Dermatol., vol. 102, pp. 781–788 (1994).
Turksen et al, "Interleukin 6, insights to its funciton in skin . . . "; PNAS, vol. 89, pp. 5068–5072 *1992).
Hammer et al, "Spontaneous inflammatory disease in transgenic rates expressing . . . "; Cell, vol. 63, pp. 1099–1112 (1990).
Valdimarsson et al, "Psoriasi: a T–cell mediated autoimmunie disease induced by streptococcal superatigens?"; Immunology Today, 16(3), pp. 145–149 (1995).
Strange et al, "Interferon gamma–treated keratinocytes activate T–cells in the presence . . . "; J. Invest. Dermatol., vol. 102, pp. 150–154 (1994).

(List continued on next page.)

Primary Examiner—Scott D. Priebe
Assistant Examiner—Anne-Marie Baker
(74) Attorney, Agent, or Firm—Nixon & Vanderhyde P.C.

(57) ABSTRACT

A nucleic acid construct comprising a promoter capable of directing expression in the suprabasal cells of the epidermis and means to cause expression of an integrin subunit in the suprabasal cells. Preferably the means to cause expression of an integrin subunit is an integrin subunit coding sequence. A transgenic animal which expresses an α subunit and a β subunit of integrin in the suprabasal cells of the epidermis and methods for making the transgenic animals. At least some of the transgenic animals are useful models of human disease, especially psoriasis. A method of treating psoriasis comprising administering to the patient a compound which modulates integrin function.

14 Claims, 17 Drawing Sheets

OTHER PUBLICATIONS

Vassar & Fuchs, "Transgenic mice provide new insights into the role of . . . "; Genes & Devel., vol. 5, pp. 714–727 (1991).

Vogel et al, "Transcriptional activation of psoriasis–associated cytokeratin K–17 by interferon–γ"; Eur. J. Biochem., vol. 227, pp. 143–149 (1995).

Lee et al, "Interleukin–1α mediates phorbol ester–induced . . . "; FASEB J., vol. 8, pp. 1081–1087 (1994).

Fierlbeck et al, "Psoriasis induced at the injection site of recombinant Interferon Gamma"; Arch. Dermatol., vol. 126, pp. 351–355 (1990).

Hotchin et al, J. Cell. Sci., vol. 106, pp. 1131–1138 (1993).

Rothnagel et al, "Development of an epidermal specific expression vector . . . "; J. Invest. Dermatol., vol. 94, p. 573 (1990).

Bailleul et al, "Skin hyperkeratosis and papilloma formation in transgenic mice expressing . . . "; Cell, vol. 62, pp. 697–708 (1990).

Yoneda et al, "Overexpression of human loricrin in transgenic mice produces . . . "; PNAS, vol. 90, pp. 10754–10758 (1993).

Watt & Jones, "Expression and function of the keratinocyte integrins"; Development Suppl., pp. 185–192 (1993).

Jones et al, "Integrin expression in normal, hyperplastic, dyplastic and malignant oral epithelium"; J. Pathol., vol. 169, pp. 235–243 (1993).

Hertle et al, "Aberrant integrin expression during epidermal . . . "; J. Clin. Invest., vol. 89, pp. 1892–1901 (1992).

Watt & Hertle, "Keratinocyte integrins"; The Keratinocyte Handbook, pp. 153–164 (1994).

Elder et al, J. Invest. Dermatol., pp. 24S–27S (1994).

Baadsgaard et al, J. Invest. Dermatol., vol. 95, pp. 32S–34S (1990).

Hotchin & Watt, J. Biol. Chem., vol. 267, pp. 14852–14858 (1992).

Eckert & Green, Cell, vol. 46, pp. 583–589 (1986).

Takada & Hemler, J. Cell Biol., 109(1), pp. 397–407 (1989).

Takada et al, J. Cell Biol., vol. 115, pp. 257–266 (1991).

Argraves et al, J. Cell Biol., vol. 105, pp. 1183–1190 (1987).

Hogervorst et al, Eur. J. Biochem., vol. 199, pp. 425–433 (1991).

Schnapp et al, J. Cell Sci., vol. 108, pp. 537–544 (1995).

Palmer, J. Cell Biol., vol. 123, pp. 1289–1297 (1993).

Altruda et al, Gene, vol. 95, pp. 261–266 (1990).

Suzuki & Naitoh, EMBO J., vol. 9, pp. 757–763 (1990).

Giancotti & Ruoslahti, Cell, vol. 60, pp. 849–859 (1990).

Carroll & Taichman, J. Cell Sci., vol. 103, pp. 925–930 (1992).

Williams, Pathol. Biol., vol. 40, pp. 813–821 (1992).

Mazur et al, J. Lab. Clin. Med., vol. 124, pp. 589–599 (1994).

Cheng et al, J. Med. Chem., vol. 37, pp. 1–8 (1994).

Brooks et al, Science, vol. 264, pp. 569–571 (1994).

Carrol et al, "Tissue– and stratum–specific expression of . . . ", PNAS, vol. 90, pp. 10270–10274 (1993).

Baker & Fry, "The immunology of psoriasis"; Brit. J. Dermatol., vol. 126, pp. 1–9 (1992).

Carrol et al, "Suprabasal integrin expression in the epidermis of transgenic . . . "; Cell, vol. 83, pp. 957–968 (1995).

* cited by examiner

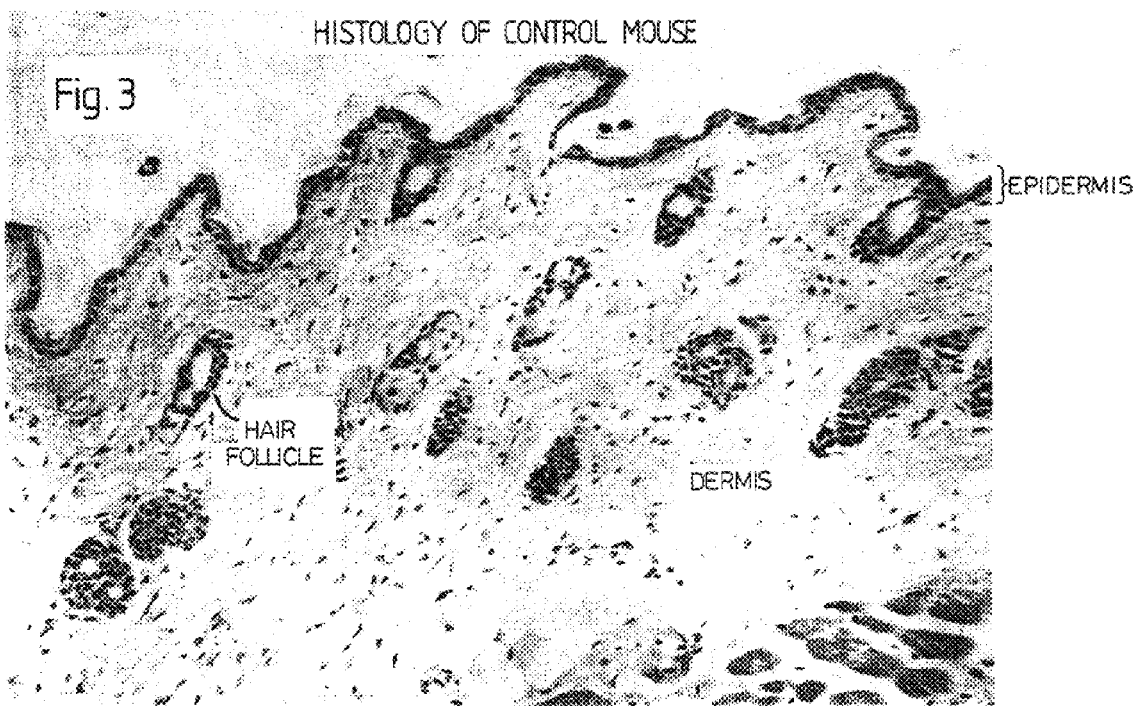

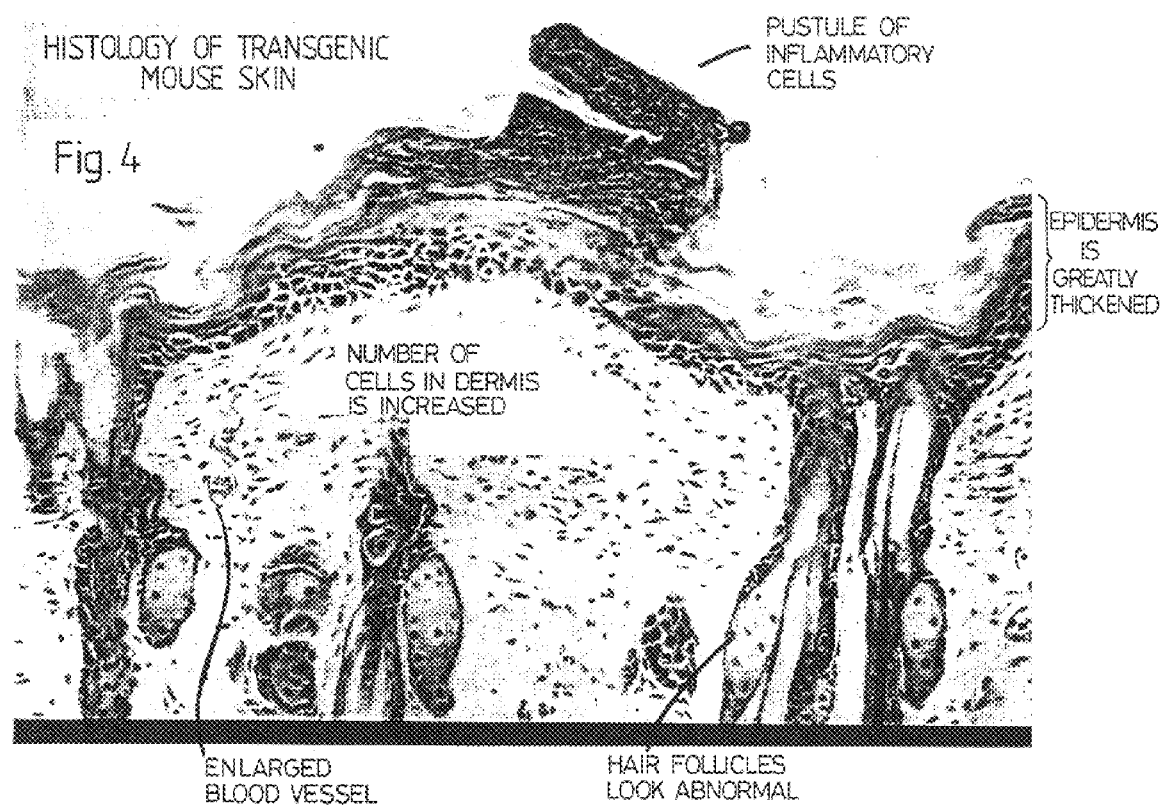

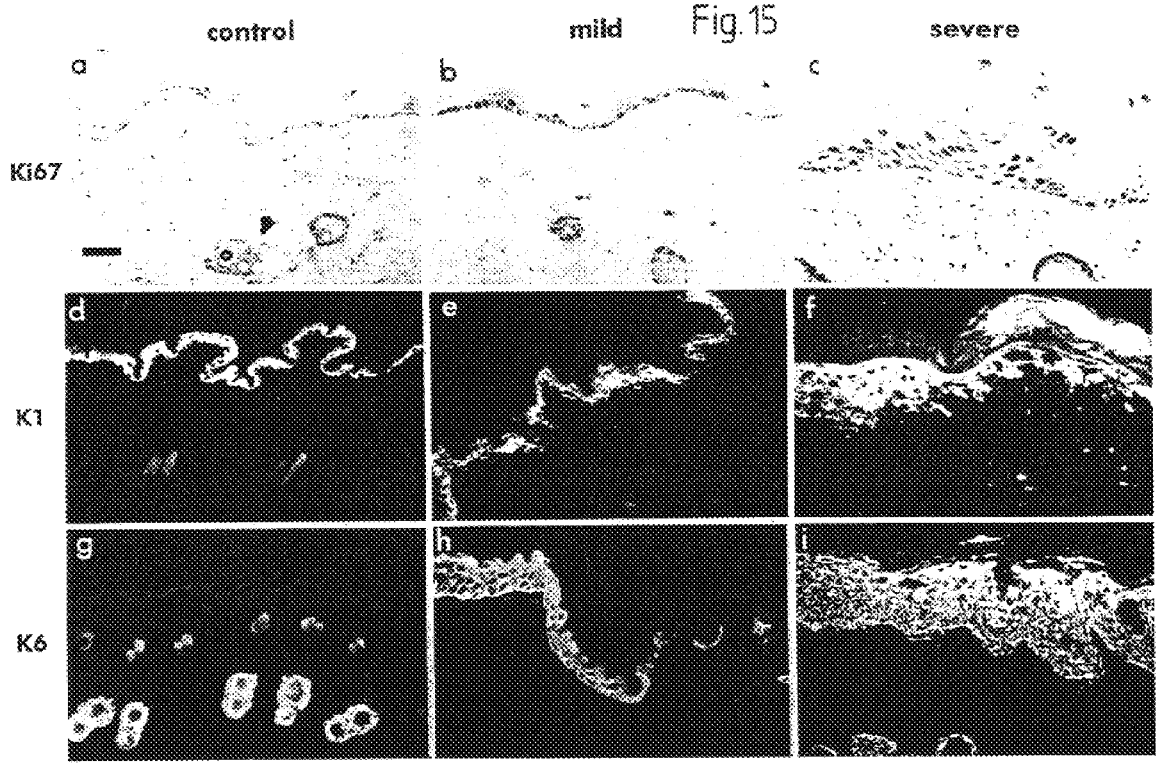

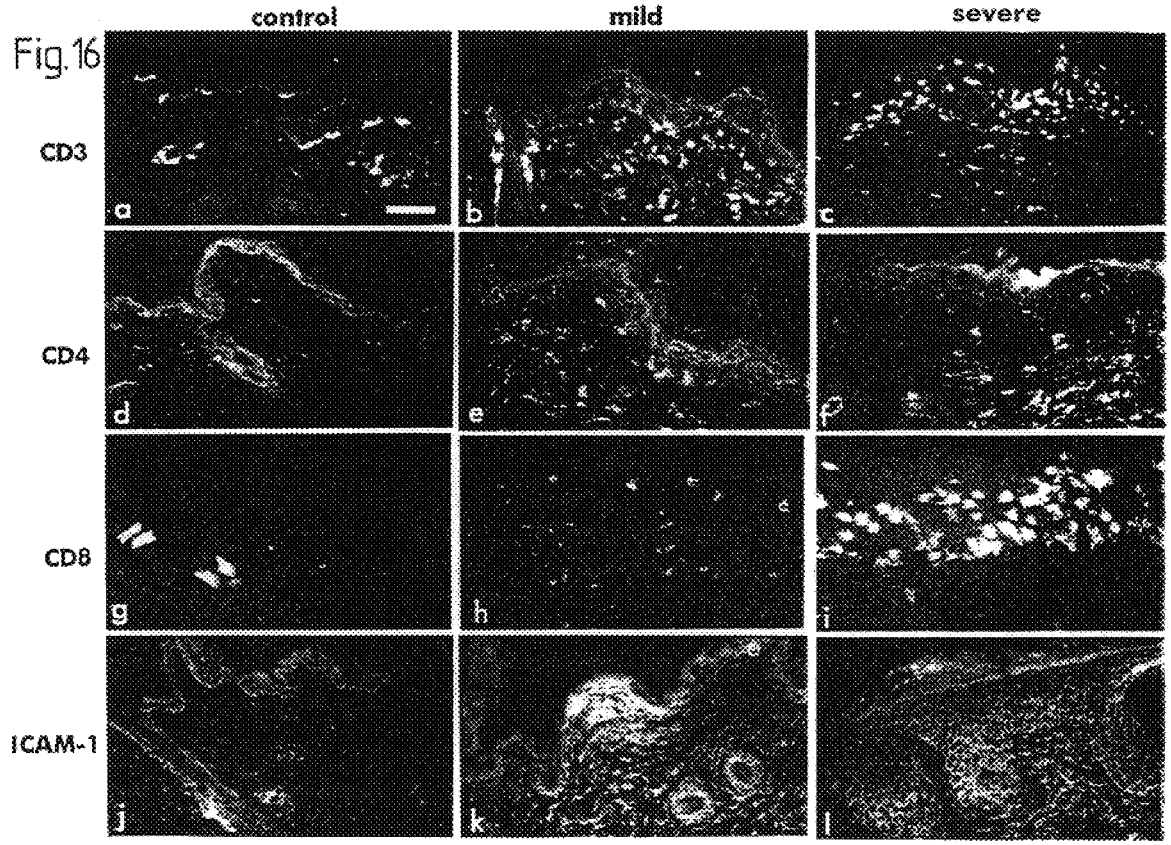

TRANSGENIC ANIMALS AS MODEL OF PSORIASIS

The present invention relates to transgenic animals which can act as a model for a human disease state. In particular, the invention relates to transgenic mammals which can serve as a non-human model for psoriasis.

Psoriasis is a skin condition that affects around 2% of the world's population and is characterized clinically by the presence of rounded, circumscribed, erythematous, dry, scaling patches of various sizes, covered by greyish white or silvery white, umbilicated and lamellar scales, which have a predilection for the exterior surfaces, nails, scalp, genitalia and lumbosacral region.

Although in its mildest form it may merely be a nuisance which it is desirable to control for cosmetic reasons, in more severe forms it can lead to severe pustule and scab formation and may be associated with arthritis.

In the earliest stages of psoriasis mild epidermal hyperplasia occurs, including mis-expression of keratins 6 and 16, and increased proliferation in the basal layer. Capillaries in the dermis become enlarged due to immune infiltrate, and mild inflammation is noticed in the epidermis as well as the dermis. The numbers and types of localised T-cell present are increased in both these tissues. In epidermis, regions of parakeratosis alternate with regions of hyperkeratosis. Mitotic activity in the dermis also has been found to increase.

In the later stages of psoriasis inflammation increases in the epidermis to the point where pustules or cysts often develop. This increased inflammation results in flaking, reddened skin. In the most generalised forms of psoriasis, marked acanthosis occurs in the epidermis, that is bell-shaped fingers of dermis invaginate the overlaying epidermis to the point where the epidermis becomes very thin focally. Also, focal necrosis of epidermal tissue may result in more severe pustule and scab formation.

Human epidermal keratinocytes express several adhesive receptors that belong to the integrin family of $\alpha/\beta$ heterodimers. Several of the keratinocyte integrins share a common $\beta_1$ subunit: $\alpha_2\beta_1$ mediates binding to collagen and laminin; $\alpha_3\beta_1$ is a receptor for laminin and epiligrin; and $\alpha_5\beta_1$ is the keratinocyte fibronectin receptor. The cells also express $\alpha_v\beta_5$, which is a vitronectin receptor, and $\alpha_6\beta_4$, which is a component of hemidesmosomes and $\alpha_8\beta_1$ and $\alpha_9\beta_1$. $\beta_1$ integrins not only mediate keratinocyte adhesion to extracellular matrix proteins, but also play a role in intercellular adhesion, lateral migration, stratification, proliferation and the regulation of terminal differentiation.

Integrin expression is largely confined to the basal, proliferative, layer of keratinocytes both in adult skin and during embryonic development (Hertle et al (1992) *J. Clin. Invest.* 89, 1892–1901). The absence of integrins from the surface of suprabasal, terminally differentiating cells reflects a two-stage downregulation of receptor function and expression (Hotchin and Watt (1992) *J. Biol. Chem.* 267, 14852–14858). The first stage occurs in basal keratinocytes that become committed to terminal differentiation: there is no reduction in the level of $\beta_1$ integrins on the cell surface, but the ability of the receptors to bind extracellular matrix proteins is substantially decreased (Hotchin and Watt (1992) *J. Biol. Chem.* 267, 14852–14858) probably reflecting a change in receptor conformation (O'Toole et al (1990) *Cell Reg.* 1, 883–893). The second stage of downregulation is the loss of integrins from the surface of cells that have left the basal layer (Hotchin and Watt (1992) *J. Biol. Chem.* 267, 14852–14858). Although integrin expression is normally confined to basal keratinocytes, there are situations in which suprabasal keratinocytes co-express integrins (reviewed by Watt and Hertle (1994) in *The Keratinocyte Handbook*, eds. I. M. Leigh, E. B. Lane and F. M. Watt, Cambridge University Press), notably during wound healing (Jones et al (1993) *J. Pathol.* 169, 235–244), in psoriatic lesions (Hertle et al (1992) *J. Clin. Invest.* 89, 1892–1901) and in some squamous cell carcinomas (Jones et al (1993) *J. Pathol.* 169, 235–244. Suprabasal integrin expression can be transient: in the healing of small suction blister wounds it occurs at the-time of wound closure, when the keratinocytes are hyperproliferative, but returns to normal one week later (Hertle et al (1992) *J. Clin. Invest.* 89, 1892–1901). Suprabasal expression is not a direct response to inflammation since it is not induced by intradermal injections of TNF$\alpha$ or IFN$\gamma$ (Hertle et al (1995) *J. Invest. Dermatol.* 104, 260–265). Suprabasal integrin expression has also been noted in eczema and lichen planus.

Genetic factors have been implicated in the epidemiology of psoriasis (Elder et al (1994) *J. Invest. Dermatol.* 24S–27S) and the immune system plays a role in the pathogenesis of psoriasis (Baadsgaard et al (1990) *J. Invest. Dermatol.* 95, 32S–34S.

At present, no-one knows what causes psoriasis.

Mild psoriasis is presently treated using an emollient. In more troublesome cases, local application of salicylic acid, coal tar, dithranol or calcipotriol can be used. Photochemotherapy using psoralens with long-wave ultraviolet irradiation is sometimes used and etretinate, a retinoid, may be given in severe or complicated psoriasis. Acitretin, a metabolite of etretinate, may also be used in severe cases, as can methotrexate and cyclosporin.

There is a need for improved treatments for psoriasis. However, no adequate model system exists for testing potential treatments. Although suprabasal expression of integrins has been found on some occasions to be associated with psoriasis (and other conditions, as noted above), there was no reason to believe that such expression could cause psoriasis, especially since the disease had been thought to have such a strong immune system involvement.

Objects of the present invention are to provide an animal model of psoriasis, means of producing such an animal model and uses for the animal model.

A first aspect of the invention provides a nucleic acid construct comprising a promoter capable of directing expression in the suprabasal cells of the epidermis and means to cause expression of an integrin subunit in the suprabasal cells.

By "means to cause expression of an integrin subunit in the suprabasal cells" we include an integrin subunit coding region and other coding regions whose expression in the suprabasal cells causes expression of an integrin subunit in the suprabasal cells. It is particularly preferred if the means to cause expression of an integrin subunit in the suprabasal cells is an integrin subunit coding region.

It is preferred if the nucleic acid construct is a DNA construct although RNA constructs, such as retroviral constructs, are included in which case the promoter is active when it is copied into DNA within a host cell.

By "a promoter capable of directing expression in the suprabasal cells of the epidermis" we include any such promoter which can so direct expression. Thus, we include promoters from animal sources, especially mammalian sources, as well as from viral sources.

A promoter which expresses in all layers of the epidermis is suitable but it is preferred if the said promoter is a keratinocyte-selective promoter, more preferably a suprabasal cell-selective promoter.

By "suprabasal cell-selective promoter" we include all nucleic acid elements that direct expression selectively in the suprabasal layer of the epidermis of an animal.

The organisation of the basement membrane, basal layer and suprabasal layer of the epidermis of a mammal is shown diagrammatically in FIG. 1.

A suprabasal cell is a cell of the epidermis. That is, if the single layer of cells adherent to the basement membrane (ie adjacent to the dermis) are defined as basal, all the other keratinocyte cells are suprabasal. A suprabasal cell is identified by its location and by expression of differentiation markers such as keratin-1, keratin-10, loricrin, filaggrin and involucrin. Suprabasal cells are found in stratified epithelia such as oral mucosa, tongue, trachea, oesophagus, cervix and vagina.

Suitable promoters therefore include the human keratin 1 promoter described by Rothnagel et al (1990) *J. Invest. Dermatol.* 94, 573 and in WO 93/22430; the bovine keratin 10 promoter described by Bailleul et al (1990) *Cell* 62, 697–708; the human loricrin promoter described by Yoneda & Steinert (1993) *Proc. Nail. Acad. Sci. USA* and in WO 93/22431; the human involucrin promoter (Carroll & Teichman (1992) *J. Cell. Sci.* 103, 925–930; Carrol et al (1993) *Proc. Natl. Acad. Sci. USA* 90, 10270–10274); and the human involucrin promoter at least part of which is described in Eckert & Green (1986) *Cell* 46, 583–589 and in EMBL/GenBank Acc. No M13902.

The human keratin 6 promoter is described in WO 93/22431. All of these documents are incorporated herein by reference.

In addition, the following gene promoters are expected to direct suprabasal cell expression: the transglutaminase gene promoter; Spr protein gene promoters (including the cornifin and pancornulin gene promoters) the cystatin A gene promoter, the promoters for the S100 protein genes, the CRAB P-II gene promoter, the filaggrin gene promoter and the promoters of the keratin 6 and keratin 16 genes. Clearly, it is likely that other gene promoters will be found that will direct suprabasal cell expression and we include these promoters.

In general, suprabasal cell-selective promoters are conserved between animals, particularly between mammals, and so suprabasal cell-selective promoters include the above named promoters from any mammal and, conveniently, from mouse, rat, rabbit, pig, cow, primates and human.

The suprabasal cell-selective promoter used in the nucleic acid construct may include more than one copy of a promoter or may contain more than one type of promoter. In addition, by suprabasal cell-selective promoter we include a promoter which does not normally direct suprabasal expression but which has been modified to do so.

In a preferred embodiment the promoter is any of the keratin 1 promoter, the keratin 10 promoter, the loricrin promoter and the involucrin promoter, for example the human or bovine version of any of these.

In a particularly preferred embodiment the promoter is the involucrin promoter, for example the human such promoter.

The suprabasal cell-selective promoter directs expression of the integrin subunit coding sequence to the suprabasal layer. By "integrin subunit coding sequence" we include a DNA sequence that encodes any subunit of an integrin.

In nature, integrins exist normally as a heterodimer of one α and one β subunit which are non-covalently associated (see Hynes (1992) *Cell* 69, 11–25 for a review). Each subunit has a large extracellular domain, a transmembrane domain and a cytoplasmic domain which is usually short and usually associates with the actin cytoskeleton. Binding of ligands, which are extracellular matrix proteins or counter-receptors of the immunoglobulin superfamily, requires both subunits; the ligand binding sites appear to be intimately associated with cation binding domains on the α subunits. So far over seven different β subunits and thirteen different α subunits have been identified and a growing number have been found to exist as two or more splice variants. An individual β subunit can potentially partner several different α subunits and vice versa; ligand binding specificity depends, to a large extent, on heterodimer composition.

Thus, we include all α integrin subunit coding regions and all β integrin subunit coding regions. The coding region may be cDNA or may contain introns.

Integrins from any source, especially from human, mouse, pig, primates, rat, rabbit, cow sources, can be used in the invention.

Particularly preferred integrin subunits are those found expressed in keratinocytes such as those described in Hertle et al (1992) *J. Clin. Invest.* 89, 1892–1901.

Preferably, when the integrin subunit is an subunit it is any of $\alpha_1, \alpha_2, \alpha_3, \alpha_5, \alpha_6, \alpha_8, \alpha_9$ or $\alpha_v$, and when the integrin subunit is a β subunit it is any of $\beta_1, \beta_4$ or $\beta_5$.

We specifically include any variants of these subunits such as those due to alternative or differential splicing, post-translational modifications or specific degradation. In particular, we include the $\beta_{1B}$ subunit.

Nucleotide sequences encoding α and β integrin subunits are well known and are publicly available from the EMBL and GenBank databases. It is well known in the art that specific DNA sequences can be amplified from suitable mRNA and DNA, for example using the polymerase chain reaction, making use of known nucleotide sequences in order to design suitable primers. Thus, integrin coding sequences (and suitable promoters) are readily available to the skilled person.

Known integrin subunit cDNAs include:

β2: EMBL/GenBank Acc. No X17033
   Reference: Takada, Y. and Hemler, M. E. (1989) *J. Cell Bio.* 109(1), 397–407

α3: EMBL/GenBank Acc. No M59911
   Reference: Takada, Y. et al (1991) *J. Cell Biol.* 115, 257–266

α5: EMBL/GenBank Acc. No X06256
   Reference: Argraves, W. S. et al (1987) *J. Cell Biol.* 105, 1183–1190

α6: EMBL/GenBank Acc. No X59512
   Reference: Hogervorst, F. et al (1991) *Eur. J. Biochem.* 199, 425–433

α8: EMBL/GenBank Acc. No L36531
   Reference: Schnapp, L. M. et al (1994) *J. Cell Sci.* (in press)

α9: EMBL/GenBank Acc. No L24158
   Reference: Palmer, E. L. (1993) *J. Cell Biol.* 123, 1289–1297

β1: EMBL/GenBank Acc. No X07979
   Reference: Argraves et al (1987) *J. Cell Biol.* 105, 1183–1190

$\beta_{1B}$: alt. β1b cytoplasmic tail: Acc. No M34189/M38176
   Reference: Altruda, F. et al (1990) *Gene* 95, 261–166

β4: EMBL/GenBank Acc. No X51841
   Reference: Suzuki, S. and Naitoh, Y. (1990) *EMBO J.* 9, 757–763

The $\alpha_5$ and $\beta_1$ cDNA are also referred to in Giancotti & Ruoslahti (1990) *Cell* 60, 849–859.

In a preferred embodiment the nucleic acid construct comprises an α integrin subunit coding sequence and a β integrin subunit coding sequence. Preferably the α and β pair is a pair that is found as a heterodimer in a keratinocyte. It is preferred if the suprabasal cell-selective promoter directs expression of both the α and β subunits to the suprabasal layer. In this preferred embodiment it is further preferred that if the β subunit is $\beta_1$ the α subunit is any of $\alpha_1$, $\alpha_2$, $\alpha_3$, $\alpha_5$, $\alpha_6$, $\alpha_8$ or $\alpha_9$; if the β subunit is $\beta_4$ the α subunit is $\alpha_6$; and if the β subunit is $\beta_5$ the a subunit is $\alpha_v$. It is most preferred that if the β subunit is $\beta_1$, the α subunit is $\alpha_2$ or $\alpha_5$.

The nucleic acid construct may contain one or more suprabasal cell-selective promoters or more than one type of suprabasal cell-selective promoter.

The nucleic acid constructs of the invention can readily be made using well known genetic engineering techniques such as these described in Sambrook et al (1989) *Molecular Cloning; A laboratory manual* (Cold Spring Harbor Laboratory Press, Plainview, N.Y.) incorporated herein by reference.

A variety of methods have been developed to operably link DNA to vectors via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn. USA.

A desirable way to modify the DNA encoding the polypeptide of the invention is to use the polymerase chain reaction as disclosed by Saiki et al (1988) *Science* 239, 487–491 incorporated herein by reference.

In this method the DNA to be enzymatically amplified is flanked by two specific oligonucleotide primers which themselves become incorporated into the amplified DNA. The said specific primers may contain restriction endonuclease recognition sites which can be used for cloning into expression vectors using methods known in the art.

A second aspect of the invention provides a host cell transformed with a nucleic acid construct, preferably DNA construct, according to the first aspect of the invention.

The host cell can be either prokaryotic or eukaryotic. Bacterial cells are preferred prokaryotic host cells and typically are a strain of *E. coli* such as, for example, the *E. coli* strains DH5 available from Bethesda Research Laboratories Inc., Bethesda, Md. USA, and RR1 available from the American Type Culture Collection (ATCC) of Rockville, Md. USA (No ATCC 31343). Preferred eukaryotic host cells include yeast and mammalian cells, preferably vertebrate cells such as those from a mouse, rat, monkey or human fibroblastic cell line. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, and monkey kidney-derived COS-1 cells available from the ATCC as CRL 1650.

As discussed in more detail below, particularly preferred host cells are animal, preferably mammalian, embryo cells which can be used to generate transgenic animals.

Transformation of appropriate cell hosts with a DNA construct of the present invention is accomplished by well known methods that typically depend on the type of vector used and the nature of the host cell. With regard to transformation of prokaryotic host cells, see, for example, Cohen et al (1972) *Proc. Natl. Acad. Sci. USA* 69, 2110 and Sambrook et al (1989) *Molecular Cloning, A Laboratory Manual*, Cold Spring Harbor Laboratory, Cold Spring Harbor, N.Y.. Transformation of yeast cells is described in Sherman et al (1986) *Methods In Yeast Genetics, A Laboratory Manual*, Cold Spring Harbor, N.Y. The method of Beggs (1978) *Nature* 275, 104–109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA.

As discussed in more detail below and in the Examples, the nucleic acid constructs, preferably DNA constructs, of the invention can be introduced into certain host cells, preferably embryo cells, by microinjection.

Electroporation is also useful for transforming cells and is well known in the art for transforming yeast cells, bacterial cells and vertebrate cells.

For example, many bacterial species may be transformed by the methods described in Luchansky et al (1988) *Mol. Microbiol.* 2, 637–646 incorporated herein by reference. The greatest number of transformants is consistently recovered following electroporation of the DNA-cell mixture suspended in 2.5×PEB using 6250V per cm at 25 μFD.

Methods for transformation of yeast by electroporation are disclosed in Becker & Guarente (1990) *Methods Enzymol.* 194, 182.

Successfully transformed cells, eg cells that contain a DNA construct of the present invention, can be identified by well known techniques. For example, cells resulting from the introduction of an expression construct of the present invention can be harvested and lysed and their DNA content examined for the presence of the DNA using a method such as that described by Southern (1975) *J. Mol. Biol.* 98, 503 or Berent et al (1985) *Biotech.* 3, 208 or the polymerase chain reaction.

Thus, in addition to the transformed host cells themselves, the present invention also contemplates a culture of those cells, preferably a monoclonal (clonally homogeneous) culture, or a culture derived from a monoclonal culture, in a nutrient medium.

The nucleic acid construct of the invention is purified from the host cell using well known methods.

For example, plasmid vector DNA can be prepared on a large scale from cleaved lysates by banding in a CsCl gradient according to the methods of Clewell & Helinski (1970) *Biochemistry* 9, 4428–4440 and Clewell (1972) *J. Bacteriol.* 110, 667–676. Plasmid DNA extracted in this way can be freed from CsC1 by dialysis against sterile, pyrogen-free buffer through Visking tubing or by size-exclusion chromatography.

Alternatively, plasmid DNA may be purified from cleared lysates using ion-exchange chromatography, for example those supplied by Qiagen. Hydroxyapatite column chromatography may also be used.

It is particularly preferred if the host cell is a non-human animal embryo cell, more preferably a non-human mammalian embryo cell. Conveniently the embryo cell is a mouse, sheep, guinea pig, rat, pig (including "mini-pig" and "micro-pig") or primate embryo cell. Mouse and pig embryo cells are particularly suitable.

A third aspect of the invention provides a method of making a transgenic non-human animal which expresses an integrin subunit in a suprabasal cell of the epidermis comprising the steps of (a) introducing into an embryo cell of the said animal a nucleic acid construct comprising a promoter capable of directing expression in a suprabasal cell of the epidermis and means to cause expression of an integrin subunit in the suprabasal cells; (b) introducing the embryo from step (a) into a pseudopregnant female animal; (c) sustaining the female in step (b) until the embryo has developed sufficiently to be independent of its mother; and (d) sustaining the said independent transgenic animal.

The animal is most suitably a mammal.

It is preferred if the means to cause expression of an integrin subunit in the suprabasal cells is an integrin subunit coding sequence.

It is preferred that >10% of suprabasal cells of the epidermis express the integrin subunit; preferably >30%; more preferably >70% and most preferably all of the suprabasal cells.

In a preferred embodiment of the third aspect of the invention in step (a) the said embryo cell contains genetic material whose presence will modify the effect of the integrin subunit in a suprabasal cell of the epidermis of the animal or wherein step (a) comprises the additional step of introducing genetic material into said embryo cell which will modify the effect of the integrin subunit in a suprabasal cell of the epidermis of the animal.

By "modify the effect of the integrin" we include modifying the effect so that the skin of the transgenic animal more closely resembles the skin of a human suffering from psoriasis.

Thus, the embryo cell may be an embryo cell from an animal with a particularly desirable genetic background. Suitably, the embryo is derived from a mutant Hairless animal such as a Hairless mouse (hairless mice are available from Sprague Dawley, Harlan UK Ltd, Shaws Farm, Blackthorn, Bicester, Oxon OX6 0TP, United Kingdom (HF1 mice), from Charles River UK Ltd, Manston Road, Margate, Kent CT9 4LT, United Kingdom (SKH1 mice) and from the Jackson Laboratory, Bar Harbor, Me. USA (HRS/J 1r/+)) so that the resultant transgenic animal has substantially no skin hair and is therefore a better model of human skin. Also suitably, the embryo is from an animal whose CD3 +γδ gene is inactivated (for example a CD3 +γδ knockout mouse wherein the T cell receptor δ gene is disrupted with a consequent loss of T cells bearing γ and δ; see Itahara et al (1993) *Cell* 72, 337–348; Tcrd mice, available from The Jackson Laboratory, is a mutant which fails to express γ and δ). There is a marked reduction in CD3 +γδ T-cells in the hyperproliferative layers and inactivation of CD3+γδ could increase the symptoms of psoriasis and provide an improved model for human psoriasis compared to an animal which is not so inactivated. Also suitably the embryo is from an animal whose CD4+/MHC class II gene is inactivated. Mice with CD4+/MHC class II inactivated are available from GenPharm International, 287 North Bernardo Avenue, Mountain View, Calif. 94043, USA and are described in Grusby et al (1991) *Science* 253, 1417–1420. Disruption of the MHC class II $a_\beta$ gene leads to a lack of cell surface MHC class II molecules and a total depletion of the CD4+ T cell population.

It is also convenient if the embryo is from an animal, particularly a mouse, in which they have a, genetic defect which -modulates MCP-1 (monocyte chemoattractant protein 1; see Nakamura et al (1995) *J. Invest. Dermatol.* 105, 635–643), B7-1 (see Williams et al (1994) *Proc. Natl. Acad. Sci. USA* 91, 12780–12784), ICAM-1 (intercellular adhesion molecule; see William & Kupper (1994) *Proc. Natl. Acad. Sci. USA* 91, 9710–9714), cpd (chronic proliferative dermatitis; see HogenEsch et al (1993) *Am. J. Pathol.* 143, 972–982), and flaky skin (fsn; see Sundberg et al (1994) *J. Invest. Dermatol.* 102, 781–788.)

In a further preferred embodiment in the additional step of introducing genetic material into said embryo cell which will modify the effect of the integrin subunit, the genetic material is any of genetic material that encodes IL-6 (interleukin 6; see Turksen et al (1992) *Proc. Natl. Acad. Sci. USA* 89, 5068–5072), HLA-B27 or $\beta_2$m ($\beta_2$-microglobulin; see Hammer et al (1990) *Cell* 63, 1099–1112), IFN-γ (interferon γ; see Strange et al (1994) *J. Invest. Dermatol.* 102, 150–154), TGF-α (transforming growth factor a; see Vassar & Fuchs (1991) *Genes & Develop.* 5, 714–727), IL-2 (interleukin-2), GM-CSF (granulocyet-macrophage colony-stimulating factor), IL-3 (interleukin-3), TGFβ (transforming growth factor β), TNFα (tumour necrosis factor α), IL-1α (interleukin 1α), and adhesion molecules such as LFA-3, CD11b and CD11c (Horrocks et al (1991) *Clin. Exp. Immunol.* 84, 157–162), and HLA-B27 (particularly when the animal is a rat; see Hammer et al (1990) *Cell* 63, 1099–1112; HLA-B27 transgenic rats are available from GenPharm International).

Thus, there are three classes of desirable genetic backgrounds. Those that make the animals a more convenient model of psoriasis in terms of testing compounds (for example, the hairless animals), those that may exacerbate the psoriasis phenotype (for example, the CD3+ γδ knockout animals), and those that may reduce the symptoms of psoriasis (for example, the CD4+ knockout animals).

It will be appreciated that in certain instances the genetic material is a nucleic acid construct as defined elsewhere in the application.

By "transgenic" animal, we include animals having a genetic construction different from the normal animal of that species. Hence, it is not necessary for the animal to have a whole gene from another species; it is enough for it to have a non-native combination of an integrin coding sequence and a control sequence such that the integrin is expressed in suprabasal cells. For example, a DNA construct comprising a human suprabasal cell-selective promoter linked to a human integrin coding sequence can be introduced into a non-human mammal such as a mouse or a pig and, as a further example, a mouse suprabasal cell selective promoter linked to a mouse integrin coding sequence can be introduced into a mouse.

It will be appreciated that when a nucleic acid construct (genetic material) is introduced into an animal to make it transgenic the nucleic acid may not remain in the form as introduced. We, nevertheless, include in the terms "nucleic acid construct" or, where appropriate, "genetic material", the term which the nucleic acid takes after entering the cell of the animal.

It is further preferred if the said promoter is a suprabasal cell-selective promoter as defined in relation to the first aspect of the invention.

Preferably, the nucleic acid construct comprises an α integrin coding sequence and a β integrin subunit coding sequence and the said independent transgenic animal expresses both the said α subunit and the said β subunit in the suprabasal cells of the epidermis.

Alternatively, but still preferably, the nucleic acid construct comprises a β integrin subunit coding sequence and the transgenic animal expresses the said β subunit in the suprabasal cells of the epidermis.

Alternatively, but still preferably, in step (a) a nucleic acid construct encoding an a integrin subunit and a nucleic acid construct encoding a β integrin subunit are introduced into the said animal embryo and the said independent transgenic animal expresses the said α subunit and said β subunit in the suprabasal cells of the epidermis.

Transgenic animals which express a β subunit or both the α and β subunit in the suprabasal cells of the epidermis will, in some cases, lead to the animal developing symptoms of psoriasis.

Mating an α-expressing animal with a β-expressing animal will produce offspring, some of which will express both the α and β integrin subunits in a suprabasal cell of the epidermis. Association of the a and fl subunits into a heterodimer will, in some cases, lead to the animal developing symptoms of psoriasis.

At least in some animals, the transgenes will be expressed suprabasally in stratified epithelia such as oral mucosa, tongue, trachea, oesophagus, cervix and vagina but psoriasis is not an issue in these tissues.

A fourth aspect of the invention provides a method of making a non-human transgenic animal which expresses an α subunit and a β subunit of integrin in a suprabasal cell of the epidermis comprising the steps of (a) mating an animal which expresses the said α-integrin subunit in a suprabasal cell df the epidermis with an animal which expresses the said β-integrin subunit in a suprabasal cell of the epidermis and (b) selecting an offspring which expresses both the said α and β subunits in a suprabasal cell of the epidermis.

It is preferred that >10% of the suprabasal cells of the epidermis express an α and a β integrin subunit; preferably >30%; more preferably >70% and most preferably all of the suprabasal cells.

A preferred embodiment of the fourth aspect of the invention is wherein one or both of the animals to be mated comprises genetic material whose presence does or will modify the effect of the integrin subunit in a suprabasal cell of the epidermis of the said offspring animal.

The genetic material whose presence does or will modify the effect of the integrin subunit is as defined in a preferred embodiment of the third aspect of the invention.

Still further aspects of the invention, related to the third and fourth aspects, provide a method of making a transgenic non-human animal which expresses an integrin subunit in a suprabasal cell of the epidermis and which contains genetic material whose presence will modify the effect of the integrin subunit in a suprabasal cell of the animal comprising the steps of (a) introducing into an embryo cell, which comprises a nucleic acid construct according to the first aspect of the invention, a nucleic acid construct whose presence does or will modify the effect of the integrin subunit in a suprabasal cell of the epidermis of the animal;

(b) introducing the embryo from step (a) into a pseudopregnant female animal; (c) sustaining the female in step (b) until the embryo has developed sufficiently to be independent of its mother; and (d) sustaining the said independent transgenic animal; and a method of making a transgenic non-human animal which expresses an integrin subunit in a suprabasal cell of the epidermis and which contains genetic material whose presence does or will modify the effect of the integrin subunit in a suprabasal cell of the epidermis of the animal comprising the steps of mating an animal which expresses an integrin subunit in a suprabasal cell of the epidermis with an animal which contains genetic material whose presence does or will modify the effect of the integrin subunit in a suprabasal cell of the epidermis of the animal and (b) selecting a suitable offspring.

By "suitable offspring" we mean an offspring that expresses said integrin subunit and which contains said genetic material.

In these further related aspects the said genetic material whose presence does or will modify the effect of the integrin subunit is as defined in a preferred embodiment of the third aspect of the invention.

It will be appreciated that in these further aspects related to the third and fourth aspects the various preferences expressed, for example the preferences of integrin subunits and animals, apply.

In both the third and fourth, and further related, aspects of the invention it is preferred if the non-human animal is a mammal. Preferred mammals include mouse, rat, pig (including "mini-pigs" and "micro-pigs") sheep, guinea pig and primates and it is particularly preferred to use mammals whose skin is similar to that of human skin.

It is particularly preferred to use mice because of their ease of manipulation and well-characterised biology and it is also particularly preferred to use pigs because of the similarity of their skin to-that of human skin.

In further preference, the pig is a "mini-pig" or a "micro-pig". Mini-pigs and micro-pigs are available from Charles Rivers Laboratories Inc, 251 Ballardvale Street, Wilmington, Mass. 01887, USA ("Mini-pig" and "Micro-pig" are trademarks). The "mini-pig" (available in Hanford and hairless Yucatan strains) will generally weigh only 30–40 kg at six months of age whereas the Yucatan "micro-pig" weighs only 14–15 kg. Thus, these pigs are more suitable for laboratory use than normal-sized pigs.

It will be appreciated that the nucleic acid constructs of the first aspect of the invention are particularly suited in the methods of the third and fourth aspects of the invention. In the preferred methods, a DNA construct is introduced into the embryo cells (preferably by microinjection) and the embryo cells are grown (conveniently in utero following implantation) to produce transgenic offspring.

Thus, once the nucleic acid constructs have been produced they are introduced into the desired mammalian embryo using, for example retroviruses or standard microinjection methods such as are described in Kraemer et al (1985), Costantini and Jaenisch, eds., *Generic Manipulation of the Early Mammalian Embryo*, Cold Spring Harbor Laboratory (bovine embryo microinjection); Hammer et al (1985) *Nature* 315, 680 (rabbit, sheep, and porcine embryo microinjection); and Gordon and Ruddle (1984) *Methods in Embryology* 101, 411 (mouse embryo microinjection). Germ-line transformation of mice is also described by Palmiter & Brinster (1986) *Ann. Rev. Genet.* 20, 465–499. Microinjection is preferably carried out on an embryo at the one-cell stage, to maximize both the chances that the injected DNA will be incorporated into all cells of the animal, including skin tissue, and that the DNA will also be incorporated into the germ cells, so that the animal' offspring will be transgenic as well. Microinjection is a standard technique which involves, briefly, isolating fertilized ova, visualizing the pronucleus, and then injecting the DNA into the pronucleus by holding the ova with a blunt holding pipette of a diameter on the order of 50 µm, and using a sharply pointed pipette of a diameter on the order of 1.5 µm to inject buffer-containing DNA into the pronucleus.

Production of transgenic non-human mammals including pigs is also described in WO 94/29434; WO 94/26884; WO 94/10305; WO 94/05796; WO 94/04672; WO 93/25669; WO 93/25071; EP 0 560 156; WO 92/22646; WO 94/01040 and WO 91/05855

All of these references describing the production of transgenic animals are incorporated herein by reference.

It is preferred that the transgenic animals made by the methods of the third and fourth aspects of the invention express a β subunit of integrin, or the following pairs of α and β subunits of integrin in the suprabasal cells of the epidermis: $\alpha_1\beta_1$, $\alpha_2\beta_1$, $\alpha_3\beta_1$, $\alpha_5\beta_1$, $\alpha_6\beta_1$, $\alpha_8\beta_1$, $\alpha_9\beta_1$, $\alpha_6\beta_4$ and $\alpha_v\beta_5$.

It has been found that in animals expressing the human $\beta_1$, integrin subunit alone, the endogenous $\alpha_6$ subunit is specifically up-regulated.

It is particularly preferred if the transgenic animal expresses the $\beta_1$, subunit $\alpha_2\beta_1$ or $\alpha_5\beta_1$ pairs in the suprabasal cells of the epidermis.

Fifth, sixth and seventh aspects of the invention provide a transgenic animal which expresses an integrin α subunit or an integrin β subunit or an α subunit and a β subunit of integrin and, in each case, the said integrin subunit or subunits is or are expressed in the suprabasal cells of the epidermis. Suitably the said transgenic animal comprises an integrin subunit coding region expressibly linked to a suprabasal cell-selective promoter such that the promoter directs the suprabasal cell-selective expression of the integrin subunit. Preferred promoters are those that are preferred in the nucleic acid construct of the first aspect of the invention.

Conveniently, the transgenic animals are made by the methods of the third and fourth, and further related aspects of the invention.

A still further aspect of the invention provides a transgenic non-human animal which expresses an integrin subunit in the suprabasal cells of the epidermis and comprises genetic material whose presence will modify the effect of the integrin in a suprabasal cell of the epidermis of the animal.

It is most preferred if the transgenic animal is a mammal, the preferred mammals being those that are preferred in the methods of the third and fourth, and further related aspect of the invention.

By "transgenic" animal we also include an animal, preferably a mammal, which has had a nucleic acid construct capable of expressing a subunit of an integrin introduced into the suprabasal cells of the epidermis by application of the said construct onto, and penetrating the dead layers of, the skin. Conveniently, the nucleic acid construct is formulated so as to penetrate the dead layers of the skin and to enter the suprabasal cells. Packaged retroviruses may be a suitable form in which to deliver the nucleic acid constructs to the suprabasal cells.

Preferably, the transgenic animal which expresses an integrin α subunit expresses any of $\alpha_1$, $\alpha_2$, $\alpha_3$, $\alpha_5$, $\alpha_6$, $\alpha_8$, $\alpha_9$ or $\alpha_v$.

Preferably, the transgenic animal which expresses an integrin α subunit expresses any of $\beta_1$, $\beta_4$, and $\beta_5$.

For the transgenic animal which expresses an integrin α subunit and an integrin β subunit it is preferred that if the β subunit is $\beta_1$ the subunit is any of $\alpha_1$, $\alpha_2$, $\alpha_3$, $\alpha_5$, $\alpha_6$, $\alpha_8$ or $\alpha_9$; if the β subunit is $\beta_4$ the α subunit is $\alpha_6$; and if the β subunit is $\beta_5$ the α subunit is $\alpha_v$.

Transgenic animals which express an integrin β subunit but not an integrin α subunit are also preferred.

It is most preferred if, when the β subunit is $\beta_1$, the α subunit is $\alpha_2$ or $\alpha_5$.

It is also preferred if, when the β subunit is $\beta_1$, the αsubunit is $\alpha_6$.

A further aspect of the invention provides offspring of the transgenic animals of the invention. By "offspring" we include any product of the mating of the transgenic animal whether with another transgenic animal or not, provided that the offspring carries the transgene. In addition we include any germ cells of the transgenic animal which may be used to propagate a further animal containing a transgene which causes expression of an integrin subunit in the suprabasal cells of the epidermis.

A still further aspect of the invention includes a suprabasal cell derived from the transgenic animal and that expresses an integrin subunit. Such cells can be cultured by well known techniques and may be useful as model systems in their own right.

At least some of the transgenic animals of the invention exhibit a symptom of psoriasis. As described in the Examples, a transgenic mouse that expresses the $\alpha_2\beta_1$ and $\alpha_5\beta_1$ integrin subunit pairs and $\beta_1$ alone in the suprabasal layer of its epidermis remarkably exhibits almost all of the symptoms of human psoriasis.

In particular, the transgenic animals exhibit symptoms of psoriasis vulgaris.

Psoriasis is believed to have genetic and environmental components; our application relates to suprabasal integrin expression in animals of any genetic background and, as described above, it is possible to make the transgenic animals of the invention with particular genetic backgrounds.

Although as described above, animals with a substantially normal genetic background can exhibit a symptom of psoriasis when made transgenic with one or more integrin subunit coding regions or means to cause expression of said coding regions, the model for human psoriasis that these animals provide may be improved by producing animals (either by mating or by transgenesis as described above) which have a genetic background (either a particular mutant background or a genetic background caused by the presence of a particular transgene) which enhances the psoriasis phenotype of the animal or mimics the changes that occur normally in an animal that has psoriasis, particularly a human that has psoriasis.

In a preferred embodiment, the transgenic animals which has or can develop symptoms of psoriasis further comprise an agent which enhances the development of a symptom of psoriasis or enhances the psoriasis phenotype.

A further aspect of the invention provides a method of enhancing the development of a symptom of psoriasis or enhancing the psoriasis phenotype of a transgenic animal which has or can develop comprising the step of contacting said transgenic animal with an agent which enhances said development or said phenotype.

By "an agent which enhances the development of a symptom of psoriasis or enhances the psoriasis phenotype" we include any agent which does this. In particular, we include any one, or combination, of the following: a cytokine such as any one of IFNγ, GM-CSF, IL-1, IL-2, IL-3, IL-6, TGFα, TGFβ, TNFα; lithium, preferably in the form of a salt; phorbol esters including phorbol 12-myristate 13-acetate (PMA) and phorbol 12,13 dibutyrate (PDBu); and super antigens (for example as defined in Valdimarsson et al (1995) *Immunology Today* 16, 145) such as those derived from bacteria and include bacteriol exotoxins, especially those from Streptococcus and Staphylococcus.

Conveniently, the agent is administered by any route and may be administered systemically. It is preferred if the agent is administered topically or by injection. It is particularly preferred if the administration is at the site in the animal where the enhancement is required.

An eighth aspect of the invention provides a method of selecting a compound which ameliorates psoriasis comprising (a) administering a compound to a transgenic animal which expresses an α subunit and a β subunit of integrin in the suprabasal cells of the epidermis or a β subunit without an α subunit and which displays a symptom of psoriasis and (b) after a suitable period of time determining whether the compound reduces or eliminates the said symptom.

We include a nucleic acid as a "compound" which may be an oligonucleotide (such as an antisense oligonucleotide) or DNA or RNA which codes for a protein. We also include proteins and peptides in the term "compound".

A suitable time includes anything from about four hours to twelve weeks; preferably, about twelve hours to one week; more preferably about seventy-two hours. The compound can be administered over a period of time in which case the time after which the effect (if any) is determined may be lengthened accordingly.

The compounds may be administered by the topical, oral routes and by injection (intravenous or into the skin). Topical administration (to the skin) is preferred. It is preferred if the compound is administered in a formulation capable of penetrating the protective (dead) outer layers of the epidermis. It is preferred if the animal, preferably a mammal, is shaved prior to topical administration of the compound, although an advantage of using a pig is that it need not be shaved prior to application of the compound to be tested.

A ninth aspect of the invention provides a compound obtainable by the eighth aspect of the invention. Such compounds are useful in treating psoriasis.

The aforementioned compounds of the ninth aspect of the invention or a formulation thereof may be administered by any conventional method including oral and parenteral (eg subcutaneous or intramuscular) injection. The treatment may consist of a single dose or a plurality of doses over a period of time.

Whilst it is possible for a compound of the invention to be administered alone, it is preferable to present it as a pharmaceutical formulation, together with one or more acceptable carriers. The carrier(s) must be "acceptable" in the sense of being compatible with the compound of the invention and not deleterious to the recipients thereof. Typically, the carriers will be water or saline which will be sterile and pyrogen free.

A tenth aspect of the invention provides a use of a compound which modulates integrin function in the manufacture of a medicament for the treatment of psoriasis.

By "compound which modulates integrin function" we include, for example, compounds that bind directly to an integrin and compounds that modulate integrin function directly or indirectly.

Disintegrins, which are RGD-containing peptides found in snake venoms, inhibit integrins. For example, see the review by Williams (1992) *Pathol. Biol.* 40, 813–821. Other RGD-containing peptides can also selectively inhibit integrins (Mazur et al (1994) *J. Lab. Clin. Med.* 124, 589–599).

Similarly, anti-integrin antibodies may also inhibit integrin (Brooks et al (1994) *Science* 264, 569–571).

By "RGD-containing peptides" we mean peptides comprising the amino acid sequence Arginine-Glycine-Aspartic acid.

The term "peptide" includes any peptide which has at least 3 amino acid residues. Preferred peptides have between 4 and 1000 amino residues; more preferably between 8 and 500 amino acid residues; even more preferably between 10 and 100 amino acid residues. We include cyclic peptides, branched peptides and peptides with non-natural or non-standard amino acids such as D-amino acids, ornithine and the like.

Peptides may be synthesised by the Fmoc-polyamide mode of solid-phase peptide synthesis as disclosed by Lu et al (1981) *J. Org. Chem.* 46, 3433 and references therein. Temporary N-amino group protection is afforded by the 9-fluorenylmethyloxycarbonyl (Fmoc) group. Repetitive cleavage of this highly base-labile protecting group is effected using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalising agent). The peptide-to-resin cleavable linked agent used is the acid-labile 4hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/1-hydroxybenzotriazolemediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesised. Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from Calbiochem-Novabiochem (UK) Ltd, Nottingham NG7 2QJ, UK. Purification may be effected by any one, or a combination of, techniques such as size exclusion chromatography, ion-exchange chromatography and (principally) reverse-phase high performance liquid chromatography. Analysis of peptides may be carried out using thin layer chromatography, reverse-phase high performance liquid chromatography, amino-acid analysis after acid hydrolysis and by fast atom bombardment (FAB) mass spectrometric analysis.

Specifically included in this tenth aspect of the invention are the dimeric RGD peptides described in JP-A-06298797;

the benzene-1,3,5-tri:carbonyl tris (peptide) compounds of JP-A-06239885 (which are RGD analogues; peptides containing the RGD sequence which as bound directly or via a linker to lipid as described in JP-A-06219967; the RGD peptide derivatives described in WO 94/14775; the modified peptide derivatives described in JP-A-06157588; the peptides described in JP-A-06009687; the peptides described in WO 93/08818 such as Arg-Gly-Asp, Gly-Arg-Gly-Asp -Ser-Pro, Gly-Arg-Gly-Asp-Thr-Pro, Gly-Arg-Gly-Asp-D-Ser-Proand Gly-Arg-Gly-Asp-Asn-Pro; the peptides described in WO 92/17492; and the cyclic peptides described in WO 91/15515.

None of these compounds have previously been proposed for use in the treatment of psoriasis.

Water-in-oil microemulsions are particularly convenient ways of introducing peptides by a topical route. Such systems are described in WO 94/086105 and WO 94/08603.

It is further preferred if the inhibitory compound is an RGD-containing peptide or an anti-integrin antibody or integrin-binding fragment or variant thereof. Suitably, the compound which modulates integrin function is a compound which prevents or reduces β1 integrin subunit expression in suprabasal cells.

It is preferred if these compounds are applied to the patient topically (to the skin) and more preferably in combination with an agent that can help penetrate the outer layers of the skin.

The medicament may comprise suitable formulations of the compound.

The formulations may conveniently be presented in unit dosage form and may be prepared by any of the methods well known in the art of pharmacy. Such methods include the step of bringing into association the active ingredient (compound of the invention) with the carrier which constitutes one or more accessory ingredients. In general the formulations are prepared by uniformly and intimately bringing into association the active ingredient with liquid. carriers or finely divided solid carriers or both, and then, if necessary, shaping the product.

A further aspect of the invention provides a method of treating psoriasis comprising administering to the patient a compound which modulates integrin function.

The transgenic animals are useful for testing psoriasis therapies, both chemical and genetic (eg gene therapy) and may also be useful in mapping genetic factors contributing to psoriasis.

The transgenic animals of the invention may also be useful as a model for other inflammatory diseases and responses in the skin wound healing; as a model for certain types of cancer (particularly skin cancer and including metastases) and for breeding with other transgenic mice which express, for example, the ras oncogene or specific cytokines under the control of suprabasal promoters; as a tool for studying the development of reagents which specifically affect integrin function; as a model for studying developmental abnormalities (such as in the eyelid and hair) and as a model for studying the role of integrins in autoimmune disorders such as arthritis and multiple sclerosis; and in the analysis of integrin-based therapies.

In addition to transgenic animals expressing a β integrin subunit alone or α and β integrin subunit pairs, transgenic animals expressing an α integrin subunit alone are useful as a model as described above although such an animal is not believed to develop the symptoms of psoriasis.

The invention will now be described in more detail with reference to the following examples and figures wherein:

FIG. 3 shows a photo-microscopic cross-section through the skin of a control (non-transgenic) mouse.

FIG. 4 shows a photo-microscopic cross-section (equivalent to that in FIG. 3) through the skin of a transgenic mouse which expresses $α_2$ and $β_1$ integrin subunits in its suprabasal cells. It is notable that the number of cells in the dermis is increased; the presence of a pustule of inflammatory cells; the epidermis is greatly thickened; the blood vessels are enlarged and the hair follicles look abnormal.

Figure 5:
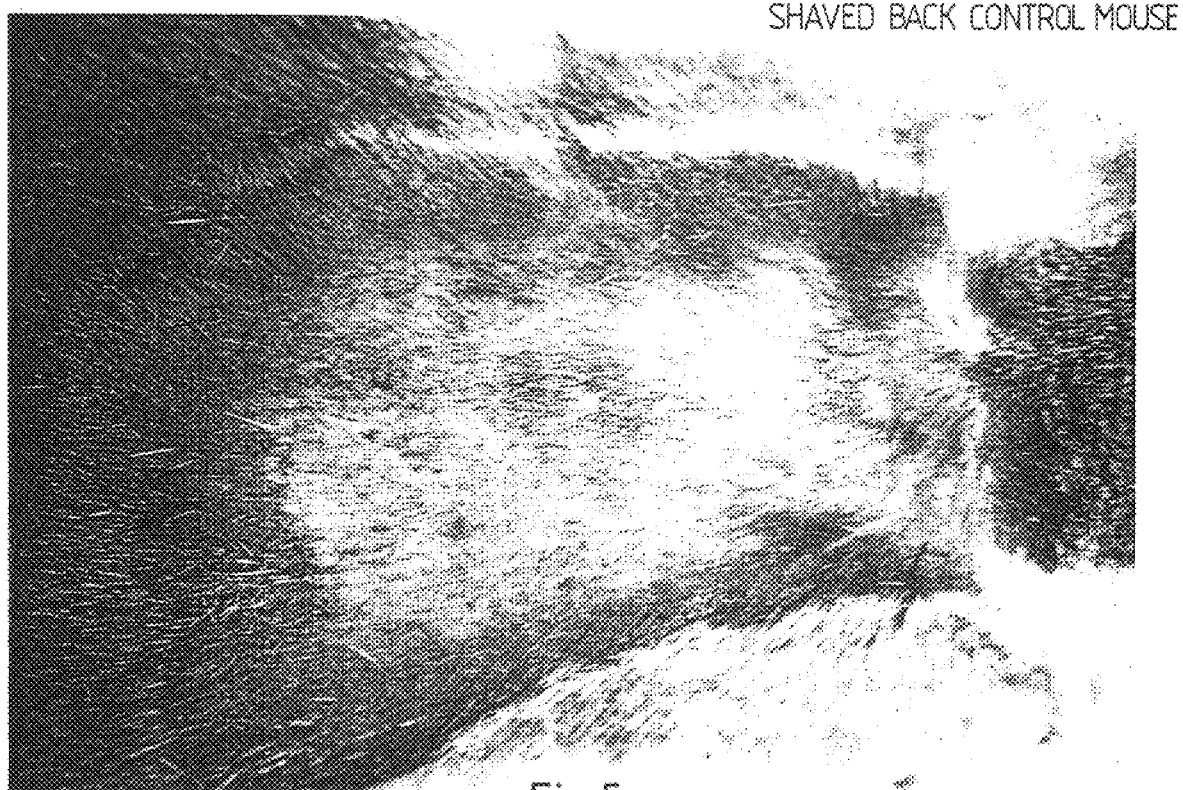

FIG. 5 is a photograph of the shaved back of a control mouse.

Figure 6:
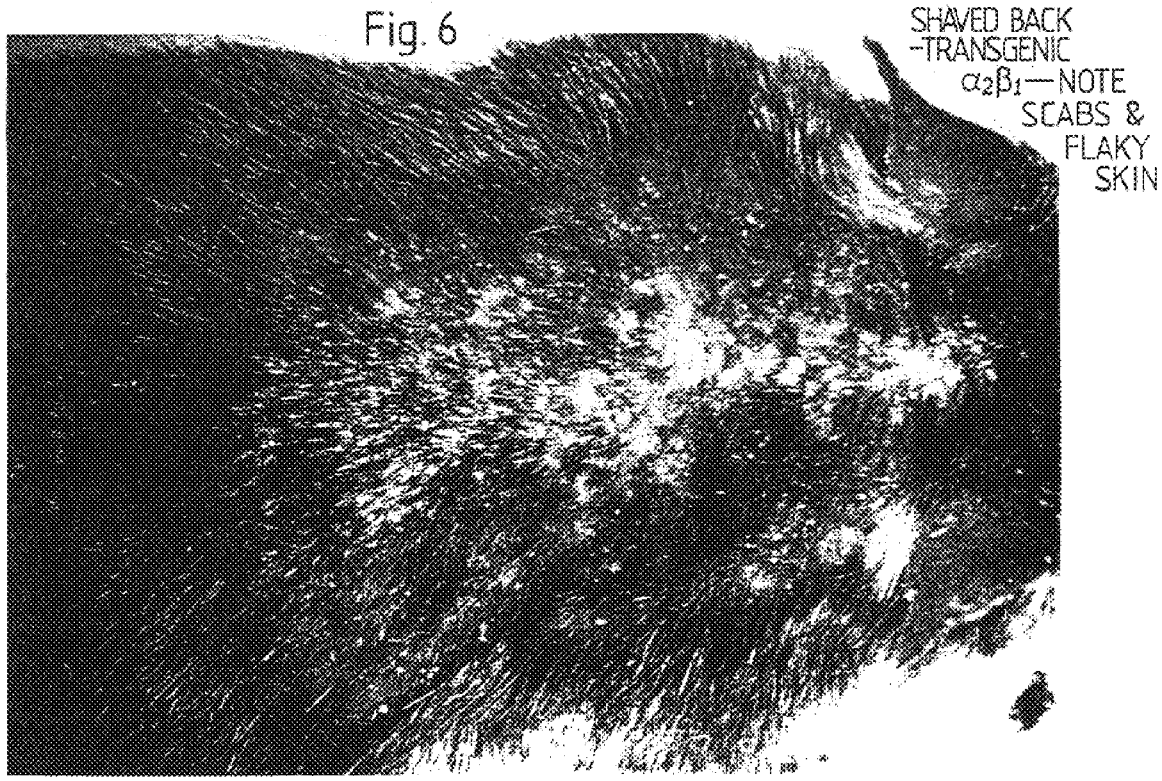

FIG. 6 is a photograph of the shaved back of a transgenic mouse which expresses $α_2$ and $β_1$ integrin subunits in its suprabasal cells. Note the scabs and flaky skin.

Figure 7:
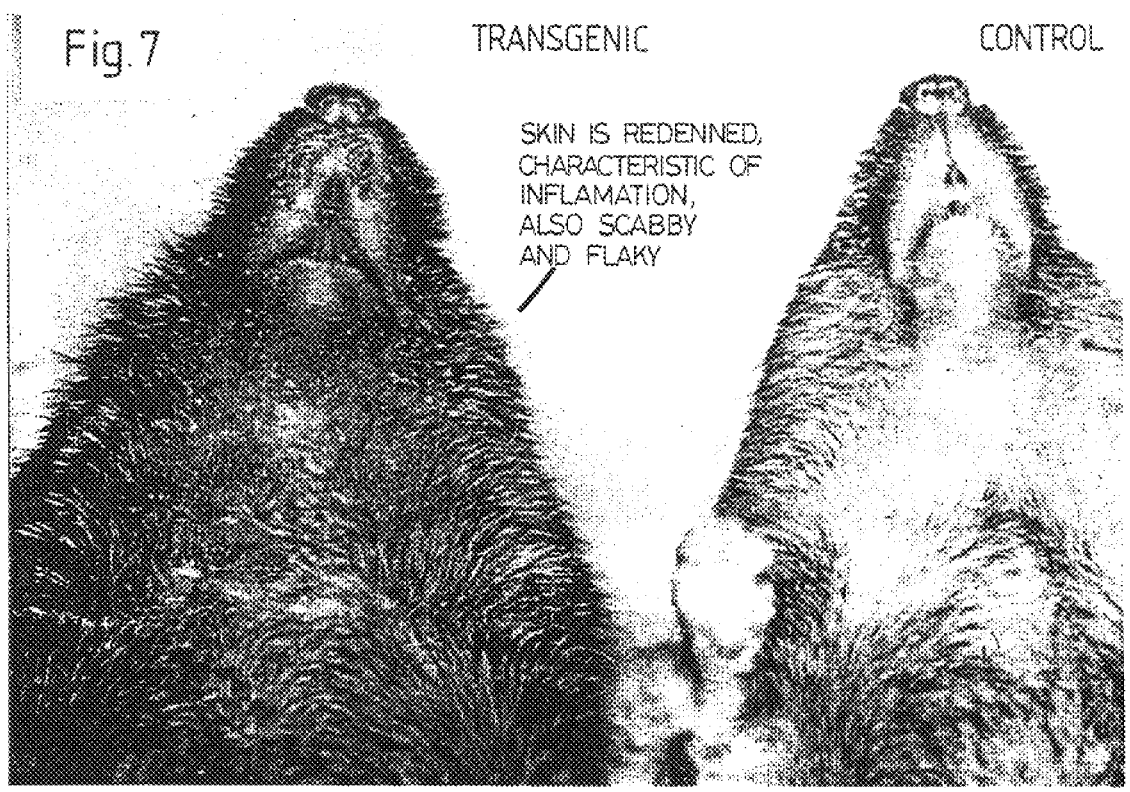

FIG. 7 is a photograph of a transgenic mouse which expresses $α_2$ and $β_1$ integrin subunits in its suprabasal cells ("$α_2β_1$") and a control mouse. There is reddening under the chin of the $α_2β_1$ mouse which is characteristic of inflammation and the mouse also has scabby, flaky skin. The control mouse does not have these features.

Figure 8:
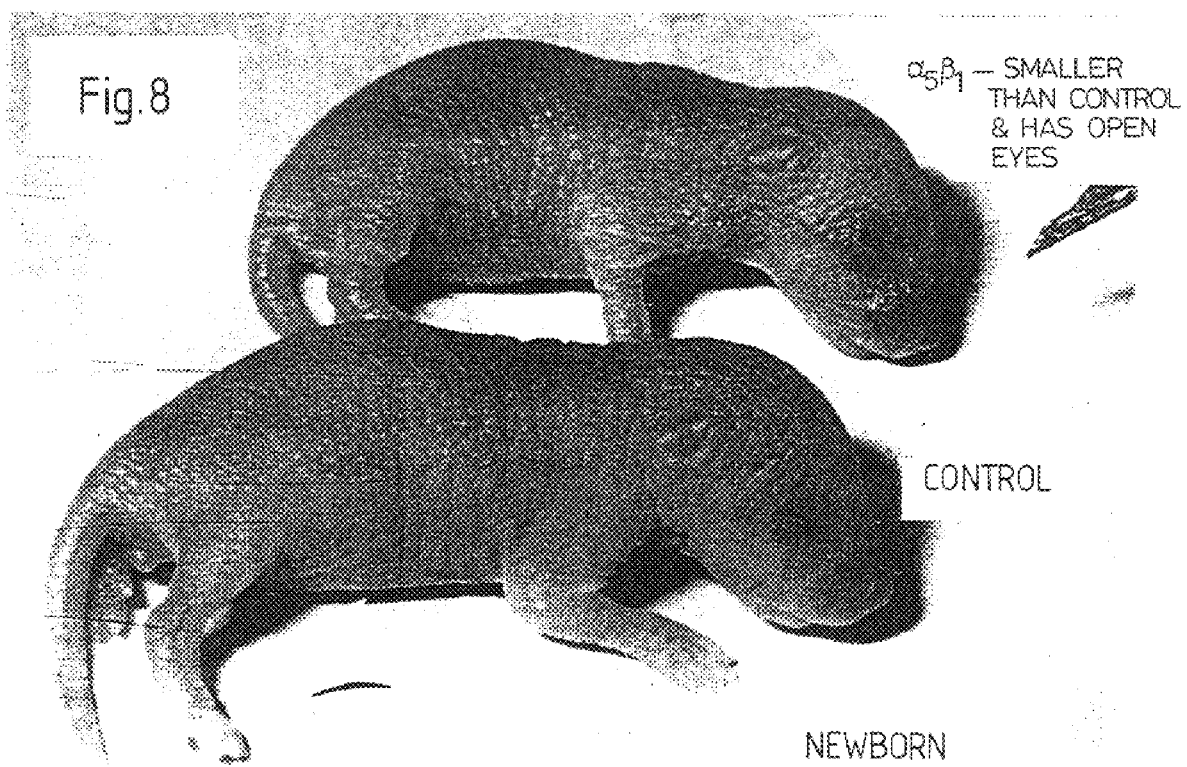

FIG. 8 is a photograph of a new born control mouse and a new born transgenic mouse which expresses $α_5$ and $β_1$ ("$αβ_1$") integrin subunits in its suprabasal cells. The $α_5β_1$ mouse is smaller than the control mouse and has open eyes.

Figure 9:
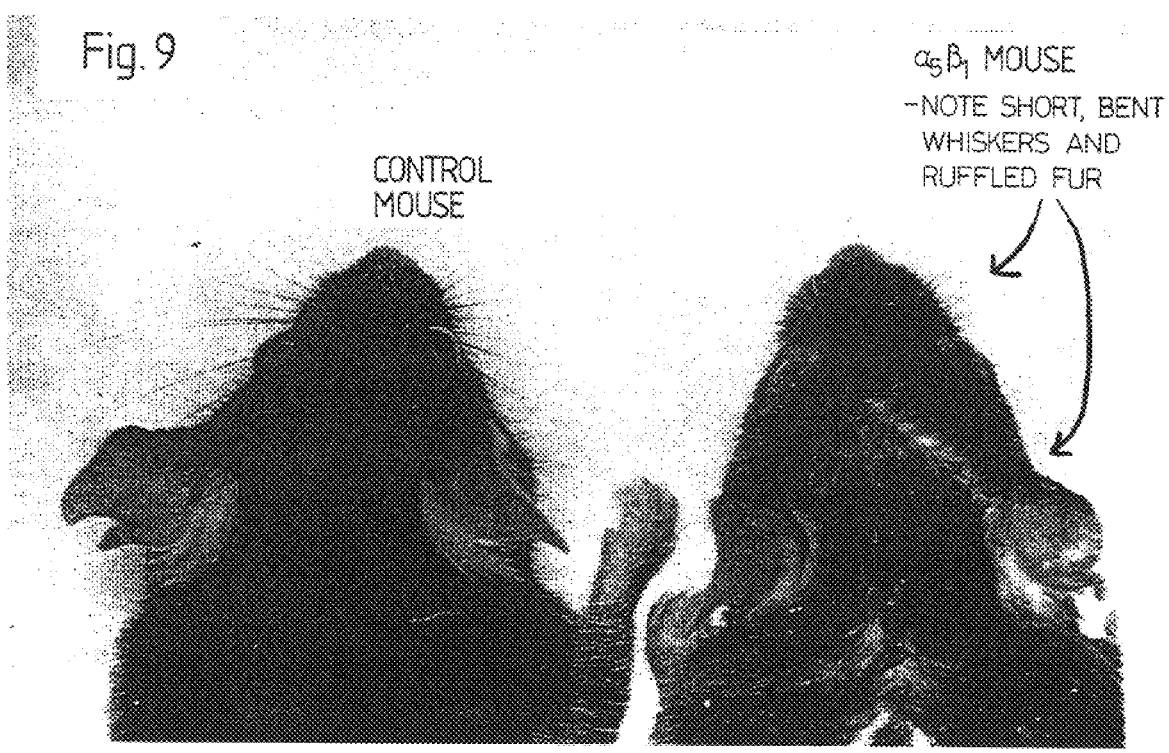

FIG. 9 is a photograph showing a control mouse and a transgenic mouse which expresses $α_5$ and $β_1$ ("$α_5β_1$") integrin subunits in its suprabasal cells. Note the short, bent whiskers and ruffled fur.

Figure 10:
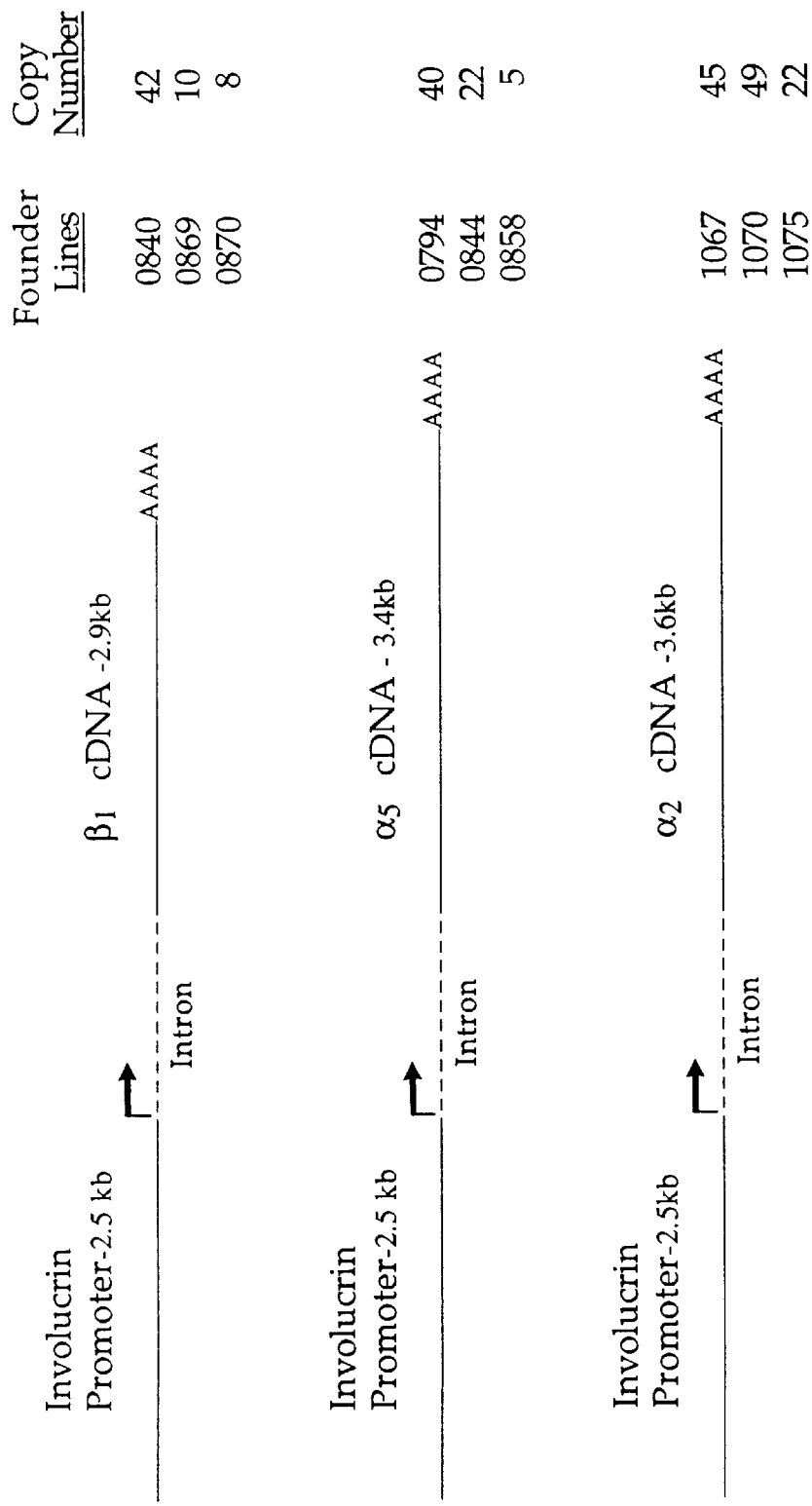

FIG. 10 shows the transgene construction and transgene copy number in each founder line.

FIGS. 11A–H illustrate integrin and involucrin expression. Sections of cheek (a,g,h) and back (b–f) skin. a): In situ hybridisation. b–h) immunofluorescence staining. (a) human $β_1$ probe, 0840 $β_1$ transgenic; b): Mouse involucrin, 0840 $β_1$ transgenic; c–e): anti-human $β_1$ antibody (CD29); c): control, nontransgenic mouse; d): 1067×0840 $α_2β_1$ transgenic mouse. e): 0840 $β_1$ transgenic mouse. f): antibody detecting mouse $β_1$ (Ha2/11), control non-transgenic mouse. g,h): antibody detecting mouse $α_6$ (GoH3); g): control, non-transgenic mouse; h): 0840 $β_1$ transgenic mouse. Scale bar: 60 μm.

Figure 12:
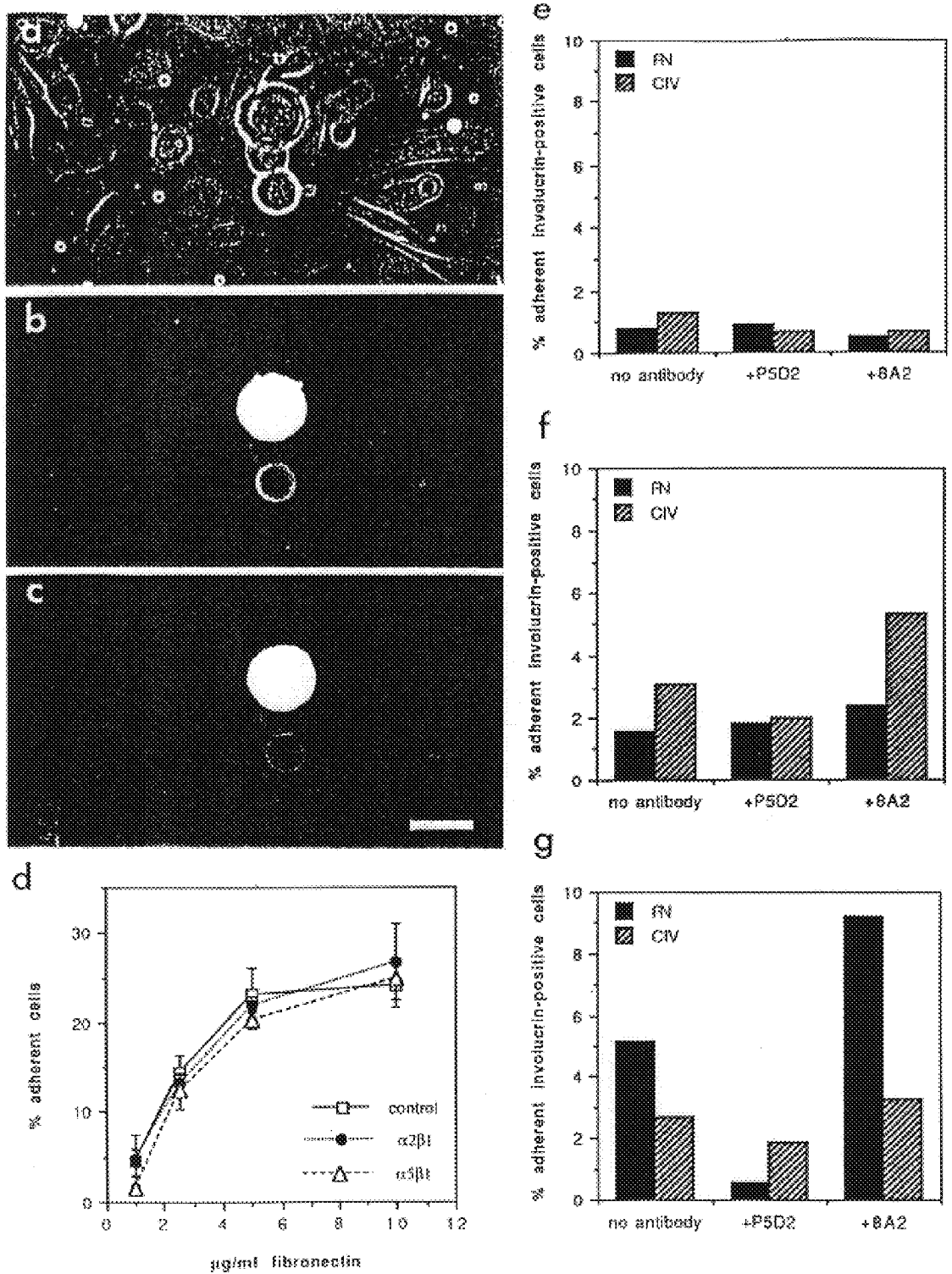

FIGS. 12$a$–$c$ shows cultured keratinocytes a–c: low calcium culture of cells from $α_2β_1$ mouse (1070×0840) a: phase contrast. b,c: double label immunofluorescence for b: involucrin, c: human $β_1$ integrin subunit. a–c: same field, scale bar=40 μm FIGS. 12$d$–$g$ show data from adhesion assays; e): nontransgenic cells; f: $α_2β_1$ cells (1070×0840); g: $α_5β_1$ cells (0794×0840). Transgenic cells in d) were from the same founder lines as in f.g). e–g) y axes: % of adherent cells that were involucrin-positive. Note that the % of involucrin-positive cells in each starting population was approximately 10%. FN: 10 μg/ml fibronectin; CIV: 10 μg/ml type IV collagen P5D2: inhibitory anti-human $β_1$ antibody; 8A2: stimulatory anti-human $β_1$ antibody. See text for $χ^2$ analysis of data in e–g. Data are pooled from duplicate (e–g) or triplicate (d) wells. d: SEM is shown.

Figure 13:
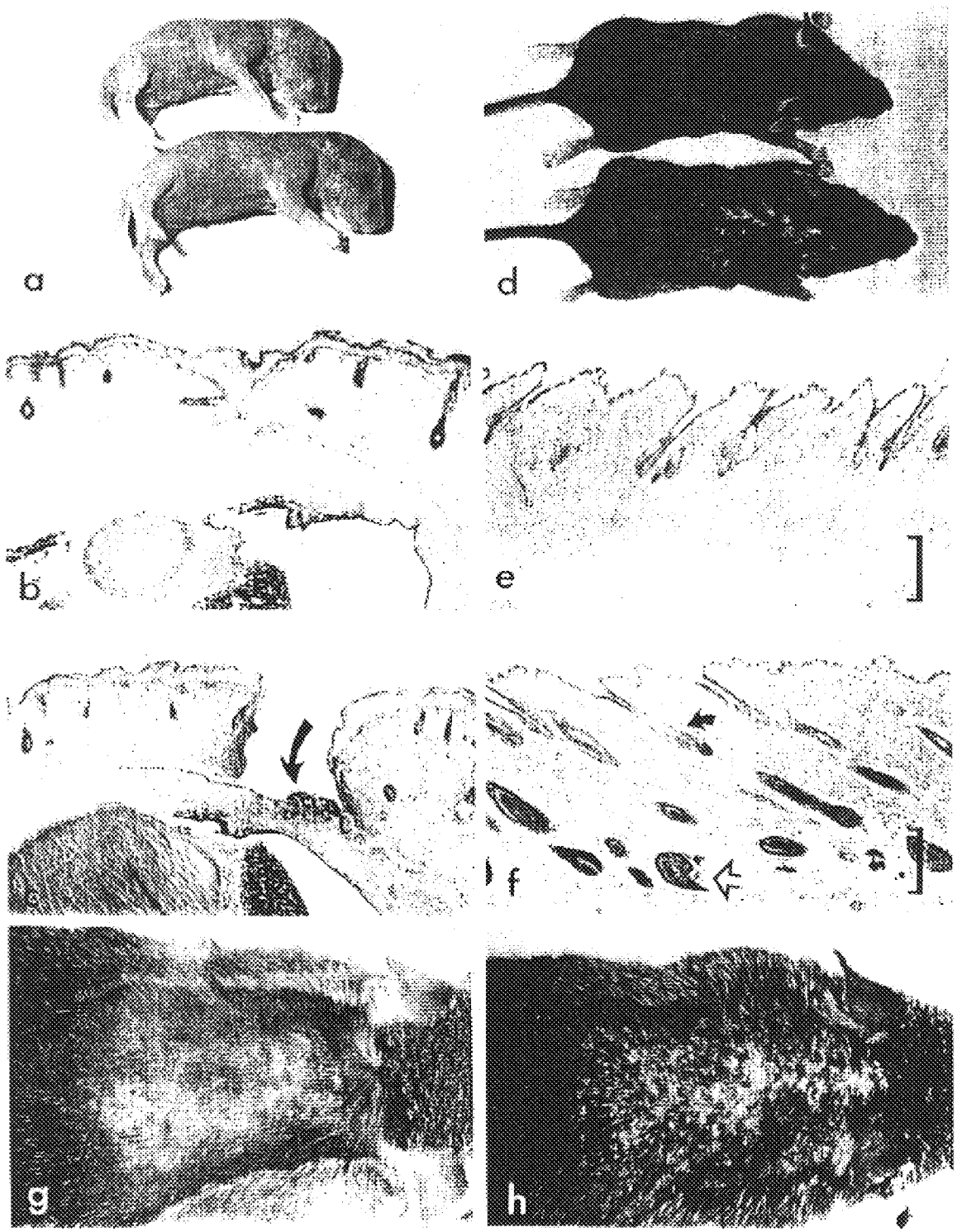

FIGS. 13$a$–$h$ show the gross phenotype of control and transgenic mice. a–c): 0.5 days after birth; a (top), c: $α_5β_1$ (0858/0869) mouse; a (bottom), b: control litter mate. b) eyelid is fused, no inflammation; c) eyelid has failed to fuse and three is an inflammatory infiltrate in the exposed region of the cornea (curved arrow) and eyelid edges. d–f: 3 months after birth; d (bottom), f: $\alpha_5\beta_1$ (0794/0840) transgenic; d (top), e: control littermate. Comparison of e,f (back skin) shows that in f) hair follicles are more deeply embedded in the dermis, have a more random orientation and abnormal morphology. g,h: shaved backs of h) 1070×0840 $\alpha_2\beta_1$ transgenic and g) control littermate, both animals aged 12 weeks b,c,e,f: haematoxylin and eosin sections. Scale bar: 100 μm.

FIGS. 14a–d show the histology of dorsal skin. Haemotoxylin and eosin stained sections. a) control, nontransgenic; b) $\beta_1$ (0840) transgenic; note thickening of epidermis to right of field with increased dermal cellularity underneath the thickened epidermis; c) $\alpha_5\beta_1$ (0794/0869); small arrows suprabasal epidermal mitoses; large arrows dilated capillaries; d): (1067/0840) curved arrow pustule in parakeratotic cornified layers. Scale bar =60 μm.

FIGS. 15a–i show the proliferation and keratin expression in back skin of (a,d,g) control, (b,c,e,f,h,i) 8040 $\beta_1$ transgenic mice. Sections of transgenic skin were chosen to illustrate mild (b,e,h) and severe (c,f,i) phenotypes. Staining in a–c: Ki67; d–f: keratin 1; g–i: keratin-6. h: Note that K6 staining is more extensive in the hyperplastic epidermis in the left of the micrograph than in the more normal epidermis in the right. Scale bar=60 μm.

FIGS. 16a–l illustrate the immune response. Sections of back skin of (a,d,g,j) control (b,e,h,k) 0794 X 0869 $\alpha_5\beta_1$ transgenic and (c,f,i,l) 1070×0840 $\alpha_2\beta_1$ transgenic mice. Sections of transgenic skin were chosen to illustrate mild (b,e,h,k) and severe (c.f.i.l ) phenotypes. Immunostaining for a–c: CD3; d–f: CD4; g–i: CD8, j–l: ICAM-1. Epidermal fluorescence in d,g,j was the same as in the sections stained with second antibody alone. Scale bar60 μm.

EXAMPLE 1

Transgenic Mice Expressing α and β Integin Subunits Suprabasally

Figure 1:
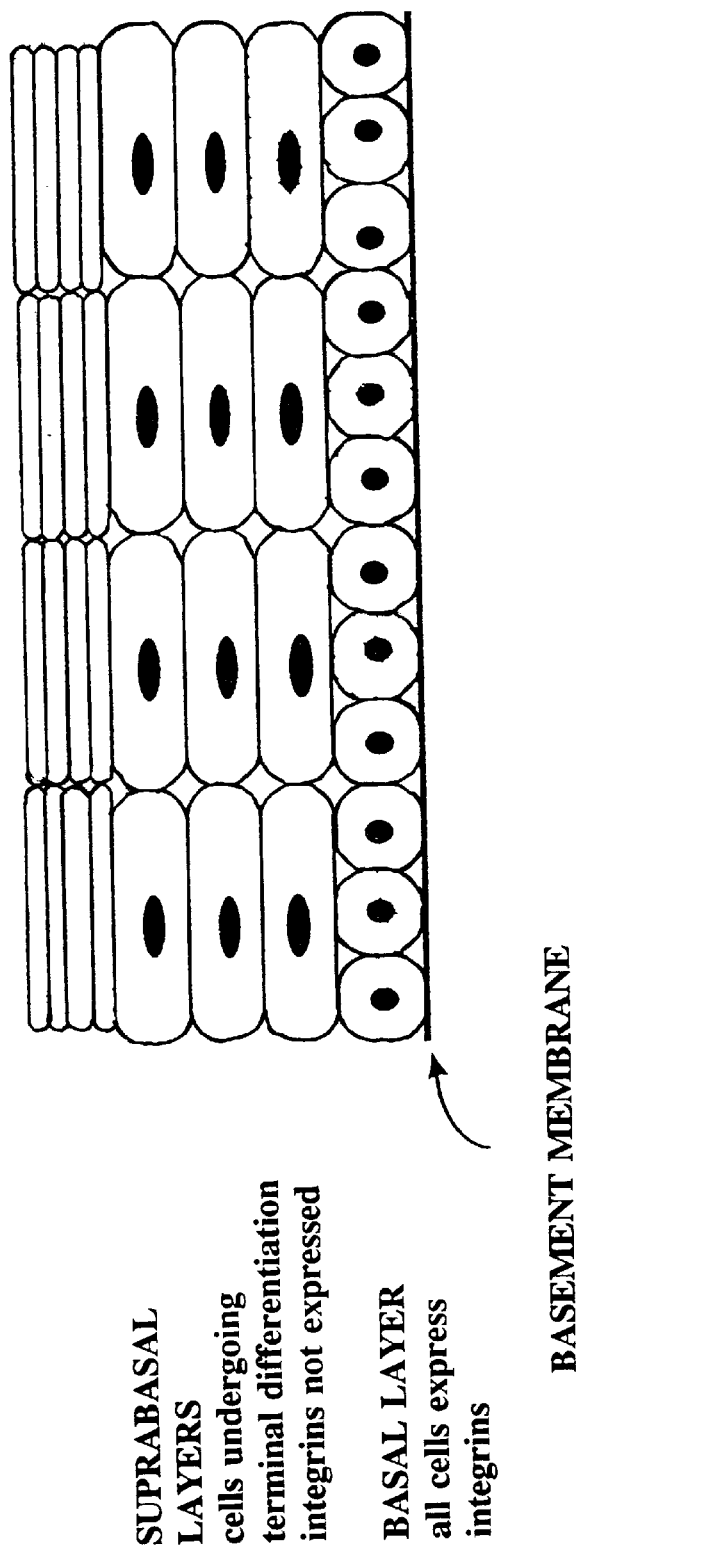
FIG. 1 is a diagram showing the arrangement of the basement membrane, basal layer and suprabasal layers of the skin.
Figure 2A:
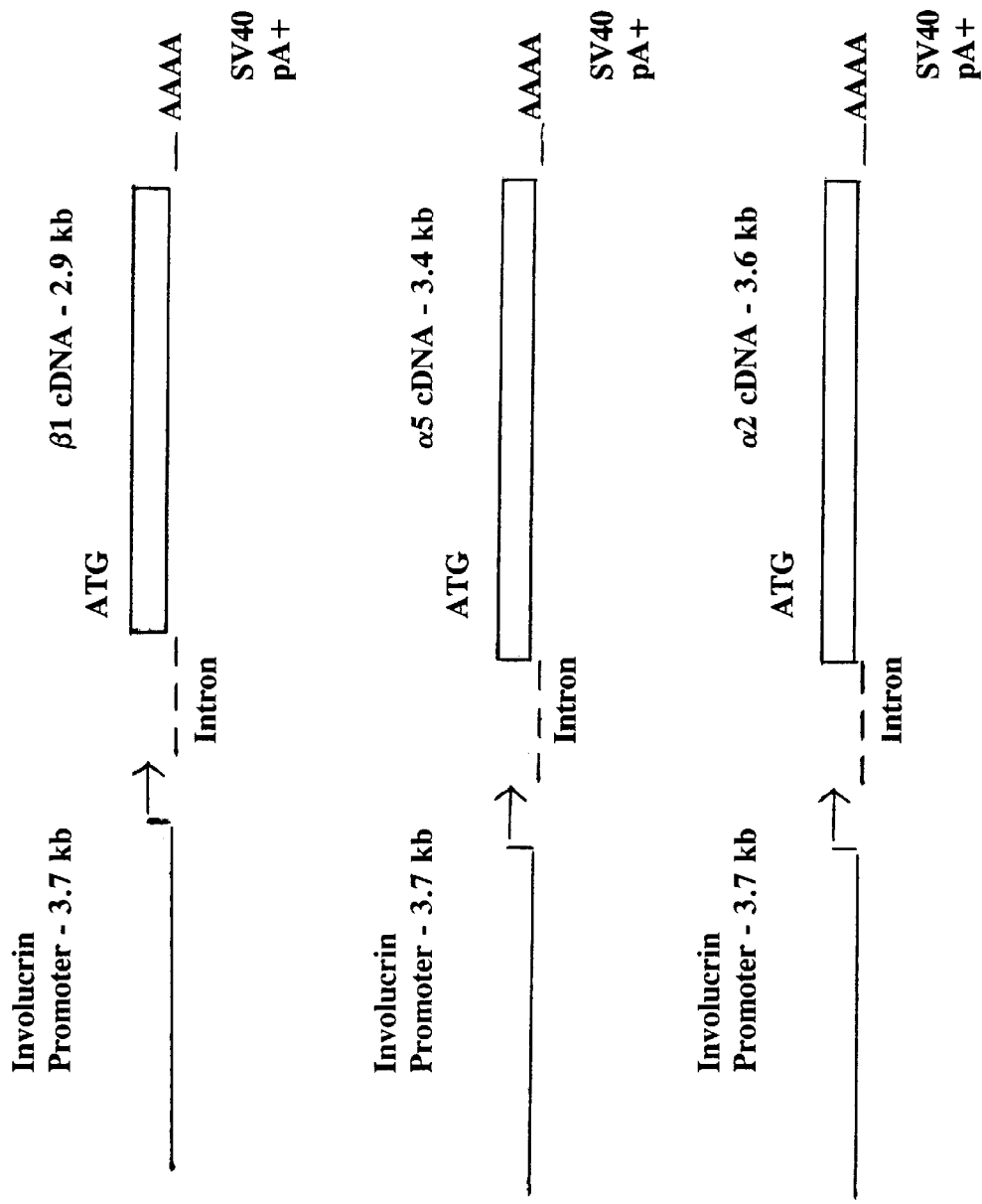
FIG. 2($a$) is a diagrammatic representation of DNA constructs containing either a $β_1$ integrin cDNA, an $α_5$ integrin cDNA or an $α_2$ integrin cDNA and, in each case, expressibly linked to the human involucrin promoter and FIG. 2($b$) is a detailed plasmid map of a vector containing the human involucrin promoter suitable for expressing an integrin cDNA.
Figure 2B:
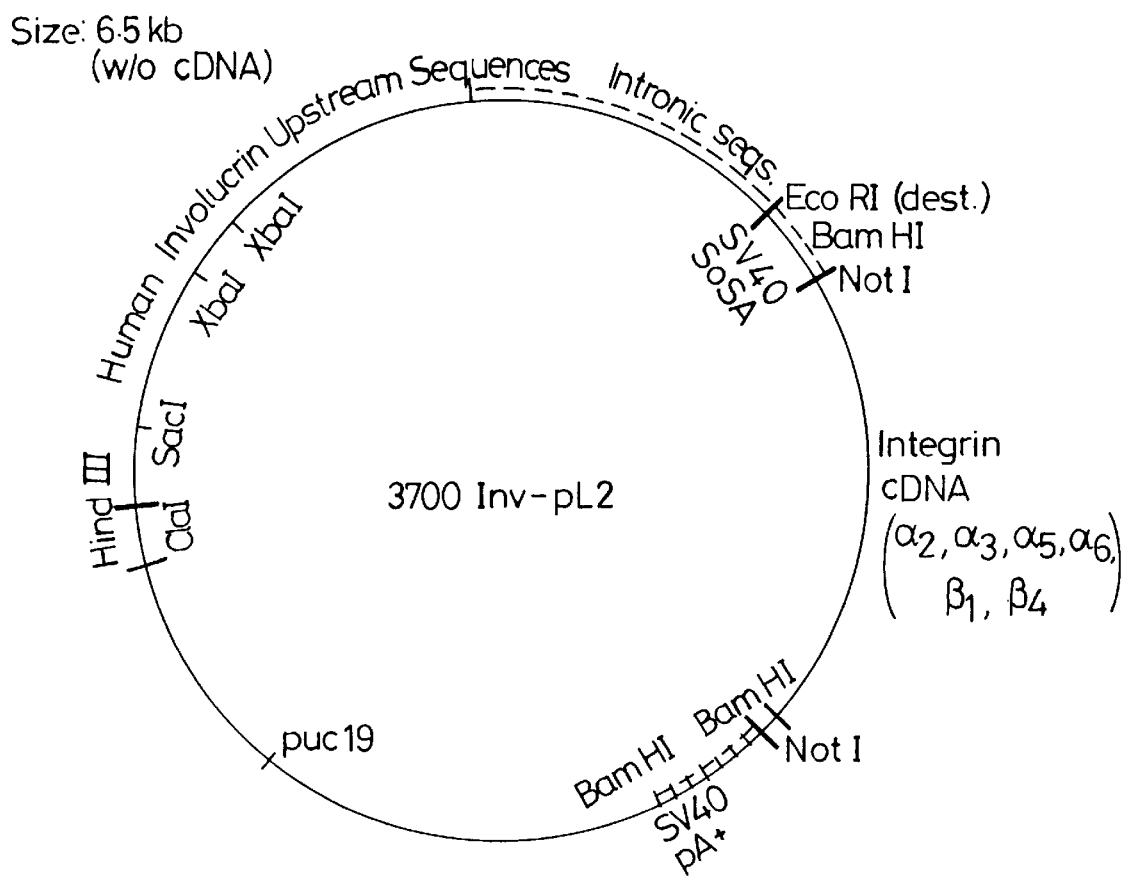

Cloning integrin cDNAs into the involucrin expression cassette: All integrin cDNA were cloned into the human involucrin expression cassette p3700-pL2 (see Carroll and Taichman (1992) *J. Cell. Sci.* 103, 925–930) at the NotI site (see FIGS. 2(a) and 2(b) for more details). Plasmid p3700-pL2 is based in the vector pNAssβ described in MacGregor (1989) *Nucl Acids Res.* 17, 2365. This plasmid contains the 3.7 kb upstream region of the human involucrin upstream region sufficient for tissue- and stratumspecificity in transgenic mice (Carroll et al (1993) *Proc. Natl. Acad. Sci.* USA 90, 10270–10274). After checking for proper orientation inserts as described above, the transgenes were separated from the backbone vector sequences by digestion with SalI restriction enzyme. The large transgene inserts were then gel-purified using Gene-Clean (Bio101), and run over a NACS-Prepac column (GIBCO-BRL). Purified was then EtOH precipitated, and resuspended in sterile PBS at a concentration of 5 μg/ml.

Integrin cDNAs suitable for insertion into p3700-pL2 are prepared as follows:

α5: The 3.5 kb cDNA was liberated from the plasmid pECE by digestion with SalI-XbaI. This fragment was gel purified, blunt-ended with Klenow enzyme and ligated to NotI linkers for insertion into the involucrin expression plasmid 3700-pL2. Potential clones were checked for orientation using the unique internal BamHI and HindIII restriction sites.

α2: The 3.8 kb cDNA was liberated from the plasmid pJ7-α2 by digestion with XbaI-KpnI. This fragment was gel purified, blunt-ended with Klenow enzyme and ligated to NotI linkers for insertion into the involucrin expression plasmid 3700-pL2. Potential clones were checked for orientation using the unique internal BamHI and SacI restriction sites.

α3: The 3.5 kb cDNA was liberated from the plasmid pBS-KSII-α3 by digestion with XbaI. This fragment was gel purified, blunt-ended with Klenow enzyme and ligated to NotI linkers for insertion into the involucrin expression plasmid 3700-pL2. Potential clones were checked for orientation using the unique internal EcoRI and HindIII restriction sites.

α6: The 3.4 kb cDNA was liberated from the plasmid pRK5-α6 by digestion with ClaI and HindIII. This fragment was gel purified, blunt-ended with Klenow enzyme and ligated to NotI linkers for. insertion into the involucrin expression plasmid 3700-pL2. Potential clones were checked for orientation using the unique internal EcoRI and XbaI restriction sites.

β1: The 3.1 kb cDNA was liberated from the plasmid pECE by digestion with EcoRI. This fragment was gel purified, blunt-ended with Klenow enzyme and ligated to NotI linkers for insertion into the involucrin expression plasmid 3700-pL2. Potential clones were checked for orientation using the unique internal HincII and HindIII restriction sites.

β4: The 5.6 kb cDNA was liberated from the plasmid pRcCMV-β4 by digestion with XbaI and HindIII. This fragment was gel purified, blunt-ended with Klenow enzyme and ligated to NotI linkers for insertion into the involucrin expression plasmid 3700-pL2. Potential clones were checked for orientation using the unique internal EcoRI and XbaI restriction sites.

Mouse Embryo Injections: The injections were carried out at the ICRF Transgenic Injection Facility. Male pronuclei of Day 1 fertilised embryos from CBA x C57BL/6 superovulated female mice were injected with the transgene using standard protocols (Hogan et al (1986) *Manipulating the mouse embryo*, Cold Spring Harbor Laboratory Press, Plainview, N.Y.). Injected embryos were then transplanted into pseudo-pregnant female mice. Approximately 6–8 weeks later, ear snips were taken from the offspring of these litters to establish founder animals. Founders were backcrossed to establish lines of animals and F1 or later generation progeny were analysed. Animals were kept on an established 12:12 hr light:dark cycle in an SPF facility. A further example of microinjection of mouse zygotes is given in Example 2.

PCR Analysis of Potential Founder Animals: PCR analysis using a previously described protocol was carried out on genomic DNA isolated from the ear snips (Carrol et al (1993) *Proc. Nati. Acad. Sci. USA* 90, 10270–10274). Primer pairs are specific for each transgene, with the 5' primer annealing to sequences within the involucrin expression cassette and the 3' primer annealing to sequences unique to each integrin cDNA. For each ear sample, PCR of endogenous actin DNA was also performed to ensure that the genomic DNA was of high integrity. Founder lines were established from PCR+ animals. As an initial screen of transgene expression, total RNA was isolated from the skin, heart and liver of control and transgene-positive animals; RT-PCR was then carried out with transgene-specific and actin primers.

To determine transgene copy number, genomic DNA was isolated from mouse tail snips and digested with restriction enzymes excising a large piece of each respective transgenic DNA. Digests were then electrophoresed on 1% agarose gels, blotted onto nylon and probed with a human involucrin DNA probe consisting of a 1.4kb SacI fragment of the involucrin upstream region. Copy numbers were determined as previously described (Carroll et al, 1993), except that an IL-2 receptor probe (single copy gene) was used to control for loading.

Breeding and Analysis of Founder Lines: Founder lines were bred through two generations to ensure transmission of the transgene and sufficient numbers of animals to analyse for expression. Once approximately 10 PCR-positive mice from each founder line were obtained, these mice were screened for integrin expression. Animals from these lines are expected to have no human transgenic integrin on the cell surface since these proteins are obligate heterodimers. Consequently, analysis was performed on RNA isolated from various tissues of the transgenic mice. Initially, total RNA was isolated using standard techniques, and RT-PCR was performed (Sambrook (1989) supra) to look for the presence of human integrin RNA in mouse tissue. RNA was also analysed using standard in situ hybridization techniques (Wilcox (1993) *J. Histochem. & Cytochem.* 41, 1725–1733). Mouse epidermal tissue from various body sites was fixed in paraformaldehyde and embedded in paraffin wax. Sections (6 $\mu$M) were hybridized with $^{35}$S-labelled riboprobes specific for each integrin subunit. Lines were screened for expression specific to the suprabasal layers of stratifying epithelia and hair follicles.

For each transgene, three separate lines exhibiting suprabasal-specific expression in stratifying epithelia and hair follicles were obtained and bred. To ensure that any phenotypes observed were specific to transgene expression, and not a random, insertional mutation, all lines were bred through and analysed. Varying degrees of expression in various lines should also result in phenotypes of varying severity. Genomic DNA from these lines is also subjected to Southern analysis to ascertain the copy number of transgene in each line.

Breeding and Cross-Mating of Mice: Because integrins are obligate heterodimers, it is necessary (if the $\alpha$ and $\beta$ constructs are not introduced into the same embryo) to mate the mice expressing the $\alpha$ and $\beta$ subunits separately in order to obtain mice expressing both integrins suprabasally. Heterozygote animals from various $\alpha$ and $\beta$ lines were bred and offspring were screened for transgene presence by PCR. Usually, about 20% of the mice within a litter are positive for both transgenes. Mice positive for both $\alpha$ and $\beta$ subunits may exhibit developmental pathologies (especially the $\alpha5/\beta1$ mice), some crosses may result in a lower viability. All mice from a given litter were kept from litters containing $\alpha/\beta$ DNA-positive mice so that sufficient numbers of control littermates could be compared with transgenic animals. Mice were monitored regularly by the staff in the ICRF SPF facility for any phenotypic anomalies.

In addition to cross-mating the mice, mice from the chosen highest expressing line of each transgenic construct were interbred to obtain a homozygote line. In this instance, approximately twelve transgene-positive mice (six males and six females) obtained from the mating of two heterozygotes were outbred to negative animals and testcrosses resulting in 100% positive offspring were considered to be homozygotes. The highest expressing line of each transgene was bred through to homozygosity to enable efficient mating as well as the opportunity to freeze embryos.

Histology, Immunofluorescence and In Situ Hybridisation

Tissues from transgenic and transgene-negative mice matched according to sex and body site were used for all tissue studies. For histological analysis, tissues were fixed overnight in formol-saline, paraffin-embedded, sectioned and stained with haematoxylin and eosin. Chloroacetate esterase was used as a histochemical marker for neutrophils.

In situ hybridisation was performed using paraformaldehyde fixed, paraffin embedded sections of mouse skin from various body sites. The probes were all $^{35}$S-labelled human integrin specific riboprobes (from pGEM4-integrin cDNA plasmids) approximately 500bp in length. Sense probes were always used as controls.

For immunofluorescence studies, mouse tissues were placed in OCT and snap frozen in an isopentane bath cooled with liquid nitrogen. Frozen sections of 8 $\mu$m thickness were cut on a cryostat. Sections were stained essentially as described (Hertle et al (1991) *J. Invest. Dermatol.* 104, 260–265) with the following modifications. After a brief fixation in acetone or paraformaldehyde sections were blocked in 5% FCS, incubated with primary antibody, washed in PBS and incubated with the appropriate fluorescein-conjugated secondary antibody. As a control sections were stained with secondary antibody alone.

For double label immunofluorescence, cultured keratinocytes were fixed in 3.7% formaldehyde, 0.4% Triton X100 in PBS for 10 min at room temperature. They were incubated simultaneously with both primary antibodies (anti-human $\beta_1$, P5D2; anti-mouse involucrin) for 1 hr at room temperature, washed in PBS and incubated with a mixture of secondary antibodies (FITC-conjugated sheep anti-rabbit IgG and Texas Red-conjugated goat anti-mouse IgG; 1 hr at room temperature), washed in PBS and mounted in Gelvatol (Monsanto Corp.).

Primary antibodies used in this study were as follows: Ha1/29 and Ha 2/11 (hamster anti-mouse $\alpha_2$ and hamster anti-mouse $\beta_1$, respectively) and 161 (rabbit anti-$\alpha_5$); HAS-6 (mouse anti-human $\alpha_2$); GoH3 anti-$\alpha_6$ (Serotec); CD29 (mouse anti-human $\beta_1$; CLB, Holland); P5D2 (mouse anti-human $\beta_1$ blocking antibody; ATCC); 8A2 (mouse anti-human $\beta_1$ activating antibody); anti-mouse involucrin (BAbCo); AF109, AF 66 (rabbit anti-mouse K1, rabbit anti-mouse K6, respectively); rat anti-CD3, CD4; CD8; CD54 (ICAM-1) (all from Pharmingen); rabbit anti-Ki67 (Novacastra).

Isolation and Culture of Mouse Keratinocytes

Mouse epidermal keratinocytes were isolated as described previously (Morris, 1994 in "Keratinocyte Methods", I. M. Leigh & F. M. Watt, eds, Cambridge University Press, pages 25–31). Briefly, adult mice were killed by $CO_2$ asphyxiation, shaved and sequentially dipped in povidone iodine solution (0.75% stock solution, diluted 1:10 in distilled water), distilled water and 70% ethanol. The skin was then removed, rinsed thoroughly in PBS containing 100 Units/ml penicillin, 100 $\mu$g/ml streptomycin and 100 Units/ml nystatin, and placed in 0.25% trypsin for 2–3 hr at 32° C. The epidermis was scraped from the dermis and stirred in calcium-free FAD (1 part Ham's F12, 3 parts DMEM, $1.8 \times 10^{-4}$ M adenine, 200 Units/ml penicillin, 200 $\mu$g/ml streptomycin) containing 10% FCS for 20 min at room temperature. Cells were filtered through a 70 $\mu$m Teflon mesh, centrifuged, and resuspended in growth medium. Cells were seeded onto vitrogen-fibronectin coated dishes. Two types of culture medium were used: SPRD-111, which is a fully defined "high calcium" medium (Morris 1994 supra), or calcium-free MEM containing 8% Chelex-treated foetal calcium serum. The MEM was supplemented as described by Miller et al (1987) *Cancer Res.* 47, 1935–1970 except that 100 Units/ml penicillin and 100 $\mu$g/ml streptomycin were used instead of gentamycin. The ionised calcium concentration in the complete MEM formulation was approximately 0.05 mM.

Adhesion Assays

For assays of the total number of cells adhering to collagen and fibronectin, bacteriological plastic 96-well microtitre plates were coated overnight at 4° C. with human type IV collagen (Sigma) or fibronectin (BioProducts Laboratory) diluted to the required concentration in PBS. Plates were then rinsed with PBS, blocked in 0.5 mg/ml heat denatured BSA (Sigma) for 1 hr at 37° C., and rinsed again with PBS before addition of cells. Keratinocytes grown in SPRD-111 medium were detached from the dishes by trypsin/EDTA treatment, washed in calcium-free FAD containing 10% FCS to inactivate the trypsin and resuspended in SPRD-111 medium. Cells were plated at a concentration of $10^4$ cells/well and incubated at 37° C. for 2 hr. Non-adherent cells were washed off and adhesion was quantitated by measuring LDH activity (CytoTox 96 non-radioactive cytotoxicity assay, Promega). Each test was performed in triplicate wells. The number of cells that attached to uncoated BSA-blocked wells was subtracted from the number of adherent cells in each experiment.

To assess the number of adherent involucrin-positive cells, keratinocytes were plated on eight well chambered slides coated with type IV collagen or fibronectin, as described above, at a concentration of $2 \times 10^4$ cells per well in the presence or absence of a human-$\beta_1$ specific blocking (P5D2; used at 250 μg/ml; ATCC; or activating antibody (10 μg/ml 8A2). After washing away non-adherent cells, the remaining adherent cells were fixed in 3.7% formaldehyde in PBS (10 min, room temperature) permeabilised in absolute methanol (5 min on ice) and immunostained with rabbit anti-mouse involucrin (BAbCo). Each test was performed in duplicate wells and the proportion of attached cells that were involucrin-positive was determined.

Analysis of Transgenic Phenotypes: Mice which were doubly positive for α and β subunits were analysed closely for basic morphology, histology, and protein expression patterns. Transgene-negative littermates matched for age and sex were always used as negative controls. Mice were examined macroscopically for defects in overall developmental, hair growth, and skin morphology from birth. Newborn animals which exhibited defects were either immediately sectioned for analysis or were examined closely through adulthood for changes in phenotype. Animals that exhibited macroscopic defects were photographed and dissected so that the epidermis from specific body sites might be analysed microscopically. Tissue biopsies were either fixed in formal saline or frozen directly in OCT embedding compound in liquid nitrogen to facilitate the cutting of frozen sections. In order to analyse overall tissue pathologies, samples in formol saline were embedded in paraffin wax, sectioned, and stained with haemotoxylin & eosin.

Sections to be used for antibody staining were cut at 6 μm on a cryostat and used without fixation. Frozen sections were reacted with antibodies to human integrins as well as endogenous mouse integrins. Sections were also screened with a panel of antibodies (eg mouse keratins, involucrin) to detect differences in epidermal differentiation and gene expression. In animals where inflammation was evident from the micropathology, a panel of antibodies to T-cells and other cells of the immune system was also used to further characterise the patterns of inflammation.

Summary of Results

The $\beta_1$, $\alpha_2\beta_1$ and $\alpha_5\beta_1$ transgenic mice were found to exhibit the following characteristics:

Mild epidermal hyperplasia and increased proliferation in the basal layer.

Capillaries in the dermis become enlarged due to immune infiltrate.

Mild inflammation is noticed in the epidermis as well as the dermis. The numbers and types of localised T-cell present are increased in both these tissues.

In epidermis, regions of parakeratosis are alternating with regions of hyperkeratosis, reflecting the changes in epidermal gene expression and differentiation.

Mitotic activity in the dermis also increases.

Inflammation increases in the epidermis to the point where pustules or cysts often develop. This increased inflammation results flaking, reddened skin.

Focal necrosis of epidermal tissue results in more severe pustule and scab formation.

Thus, they exhibit the features of human psoriasis with the exception of acanthosis. It may be that this step is a very late stage in the process or does not occur in this mouse model. The mice also mimic the human disease in site-specific-expression: that is, the severity of the disease varies with body site. The mice have the most severe phenotypes under the chin, behind the ears, around the ears, on the back of the neck, and under the legs. This is similar to human psoriasis. The average age of onset of the psoriatic phenotppe in the mice seems to be eight weeks, which for a mouse is adolescence, roughly equivalent to the mean rime of human psoriatic onset.

Photographs of $\alpha_2\beta_1$ mice (compared with control mice) are shown in FIGS. 3 to 7 and photographs of $\alpha_5\beta_1$ mice (compared with control mice) are shown in FIGS. 8 and 9.

More details are given below:

Generation of Transgenic Mice

Founder lines of transgenic mice were generated with the human $\alpha_2$, $\alpha_5$, and $\beta_1$ cDNAs cloned into an involucrin expression cassette (consisting of 2.5 kb of the human involucrin upstream region, the involucrin intron, SV40 intron and SV40 polyadenylation sequence; see FIG. 10). Potential founder animals were screened by PCR and positive animals were outbred to F1 animals to establish founder lines. Three independent lines were established for each construct. The copy number, as determined by Southern blotting, varied widely among founder lines (FIG. 10). The phenotypes described for a given transgene were seen in all the founders, although the degree of severity and penetrance varied, being greatest in the lines expressing the highest copy number, and these lines were the ones characterised in most detail.

In order to obtain mice expressing $\alpha_2\beta_1$ or $\alpha_5\beta_1$ heterodimers, animals from the $\alpha_2$ and $\alpha_5$ lines were mated with $\beta_1$ mice and progeny screened for the presence of both transgenes. Since the lines used for the crosses were not homozygous, individual litters contained animals positive for one or both transgenes, together with negative littermates which served as controls.

Expression of Transgenic and Endogenous Integrin Subunits

RT-PCR established that each founder line was expressing the appropriate human integrin subunit in the skin, but not in liver or heart. The sites of expression within the skin were determined by in situ hybridisation: the transgenes were expressed in the suprabasal layers of the epidermis (FIG. 11a) and also within the inner root sheath of the hair follicles, where the involucrin promoter has previously been shown to be active. Endogenous mouse involucrin was present in all the suprabasal layers of transgenic mouse epidermis, as judged by immunofluorescence (FIG. 11b), suggesting that the transgenic promoter was not interfering with the function of the mouse gene. No suprabasal staining for laminin 1, type IV collagen and fibronectin ($\beta_1$ integrin ligands) was observed in transgenic epidermis and the distribution of these extracellular matrix proteins in the basement membrane zone and dermis was indistinguishable in normal and transgenic mouse skin.

Figure 11:
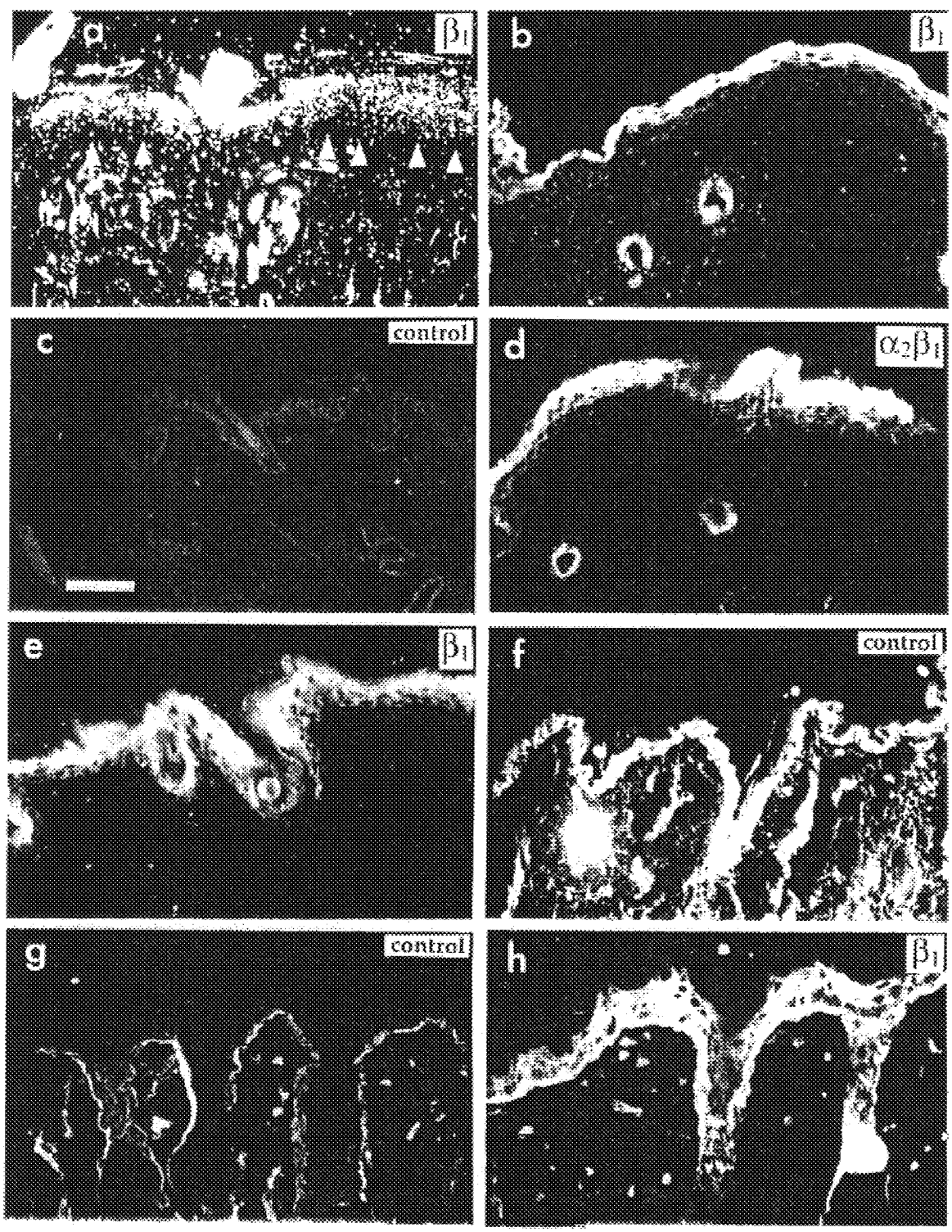

Antibodies specific for the human $\alpha_2$, $\alpha_5$ or $\beta_1$ integrin subunits stained the suprabasal epidermal layers and inner root sheath in mice expressing the corresponding transgene and did not stain nontransgenic epidermis (FIGS. 11c,d,e and results not shown). Since integrins are only expressed at the cell surface as heterodimers and the endogenous mouse integrin subunits we examined ($\alpha_2$, $\alpha_5$, $\alpha_6$ and $\beta_1$; FIGS. 11f,g and results not shown) were confined to the basal layer in normal mice, we did not expect to see cell surface human integrin in mice expressing a single transgene. However, the staining patterns observed with anti-human $\beta_1$ on epidermis from $\beta_1$, $\alpha_2\beta_1$ and $\alpha_5\beta_1$ mice were indistinguishable (compare FIGS. 11d,e). This led us to investigate whether the expression of endogenous integrin subunits was altered in mice expressing the $\beta_1$ transgene alone: mouse $\alpha_2$, $\alpha_5$ and $\beta_1$ were unaffected, but there was strong suprabasal expression of $\alpha_6$ (compare FIGS. 11g,h). Although $\alpha_6$ is expressed as a heterodimer with $\beta_4$ in mouse and human keratinocytes it is also capable of forming heterodimers with $\beta_1$. In contrast, $\alpha_6$ was not detected suprabasally in $\alpha_2\beta_1$ and $\alpha_5\beta_1$ mice.

The Transgenic Integrins are Functional Extracelular Matrix Receptors

In order to determine whether the transgenic integrins were functional we cultured keratinocytes from $\alpha_2\beta_1$ and $\alpha_5\beta_1$ mice and from control, nontransgenic littermates. In low calcium medium the keratinocytes grew as a monolayer and in post-confluent cultures, terminally differentiating, involucrin-positive cells rounded up and detached, as observed previously for human keratinocytes (FIGS. 12a,b). There was no obvious difference in cell morphology between cultures of transgenic and nontransgenic cells in low calcium medium (MEM supplemented with FCS) or in defined medium containing >1 mM calcium ions (SPRD-111) in which stratification occurred. The high plating density required in both media precluded any assessment of growth rate. Many of the transgenic keratinocytes that were involucrin-positive were also positively stained with an antibody to the human $\beta_1$ integrin subunit (FIGS. 12b,c).

Keratinocytes from $\alpha_2\beta_1$, $\alpha_5\beta_1$ and nontransgenic mice were plated on type IV collagen (the ligand for $\alpha_2\beta_1$) and fibronectin (the ligand for $\alpha_5\beta_1$) and the number of adherent cells was measured as a percentage of the total number of cells plates (FIG. 12d and results not shown). There was no significant difference in the total number of adherent cells from each type of mice (FIG. 12d), but this was not surprising, since the proportion of involucrin-positive cells in the cultures was only 10–15%. The experiments did allow us to establish that collagen and fibronectin concentrations of 10 µg/ml or greater supported maximal adhesion, and that the transgenic integrins had no effect on ligand-binding by the endogenous integrins.

When attachment of involucrin-positive cells was measured, a difference between the $\alpha_5\beta_1$ transgenic and normal mice was apparent: a greater proportion of involucrin-positive cells adhered to fibronectin in the transgenic than the nontransgenic cell populations (compare FIGS. 12e,g; p<0.0001). There was no significant difference between control and $\alpha_5\beta_1$ mice in adhesion to type IV collagen (FIGS. 12e,g). Adhesion of $\alpha_5\beta_1$ involucrin-positive cells to fibronectin could be modulated with anti-human $\beta_1$ antibodies (P5D2: inhibitory p=<0.001; 8A2, stimulatory p=0.063), while adhesion to type IV collagen could not (FIG. 12g) (p≧0.281). $\alpha_2\beta_1$ involucrin-positive cells appeared to show selective adhesion to type IV collagen (FIG. 12f), although the total number of adherent involucrin-positive cells that could be counted was lower and the results are not statistically significant. These results suggest that the transgenic integrins were -functional and that they recognised their known ligands.

Transgenic Mice have Abnormalities of Hair and Eyelids

Several abnormalities were evident from gross inspection of the mice (Table 1, FIG. 13). A significant proportion of animals expressing $\alpha_5$, $\beta_1$, $\alpha_2\beta_1$ and $\alpha_5\beta_1$ were born with open eyes and were often runted with fewer whiskers than the nontransgenic littermates (FIG. 13a). Histological sections of the eyes of newborn mice (FIGS. 13b,c) showed that there had been a failure of eyelid fusion prior to birth and that there was an inflammatory exudate in the cornea and eyelid. In adult mice there was opaqueness of the eyeball and corneal scarring.

| Summary of transgenic phenotypes | | | | |
|---|---|---|---|---|
| Transgenic Subunit(s) | open eyes at birth | whisker/hair abnormalities | epidermal hyperplasia | inflammation |
| $\alpha_2$ | 0/46 | 0/46 | 0/14 | 0/14 |
| $\alpha_5$ | 7/64 | 4/64 | 0/11 | 0/11 |
| $\beta_1$ | 25/82 | 8/82 | 14/22 | 9/22 |
| $\alpha_2\beta_1$ | 7/27 | 6/27 | 17/19 | 13/19 |
| $\alpha_5\beta_1$ | 17/23 | 18/23 | 8/11 | 4/11 |

Table 1. Animals from the 1070 ($\alpha_2$), 0794 ($\alpha_5$) and 0840 ($\beta_1$) founder lines were examined. Data were pooled from multiple litters. Hyperplasia and inflammation were assessed by examining haematoxylin and eosin stained sections of the skin of animals sacrificed 6–16 weeks after birth; mild, moderate and severe phenotypes were all scored as positive.

Adult mice expressing the $\alpha_5$ or $\beta_1$ transgenes also had abnormalities of the hairs of the coat and whiskers (Table 1, FIGS. 13d–f). The hairs of the coat did not have the uniform orientation seen in control mice and the whiskers were short and curly (FIG. 13d). The coat phenotype was seen in all sites examined (skin of the upper, middle and lower back and belly). Histological sections of the dorsal skin of mice with abnormal coat hair showed that the follicles were disorganised, abnormally orientated and extended deeper into the dermis than in control mice (FIGS. 13e,f); the morphology of individual follicles was also altered, with enlargement of the follicles themselves and of the associated pilosebaceaus glands. Individual hairs of affected animals were wavy rather than straight. The abnormal coat phenotype was apparent as soon as the first coat developed, and there was a progressive normalisation through successive hair growth cycles.

Mice expressing the $\beta_1$ transgene, alone or in combination with $\alpha_2$ or $\alpha_5$, also showed gross evidence of epidermal abnormalities and immune involvement (Table 1, FIGS. 13g,h). Scaling of the epidermis could readily be detected on the chin, behind the ears and under the limbs, or after shaving the hair from the back or belly of the animals (FIGS. 13g,h). In some mice, inflammation was seen as a reddening of the skin of chin and paws and there were pustules on the surface of the dorsal skin (FIG. 13h).

Epidermal Proliferation and Terminal Differentiation

Figure 14:
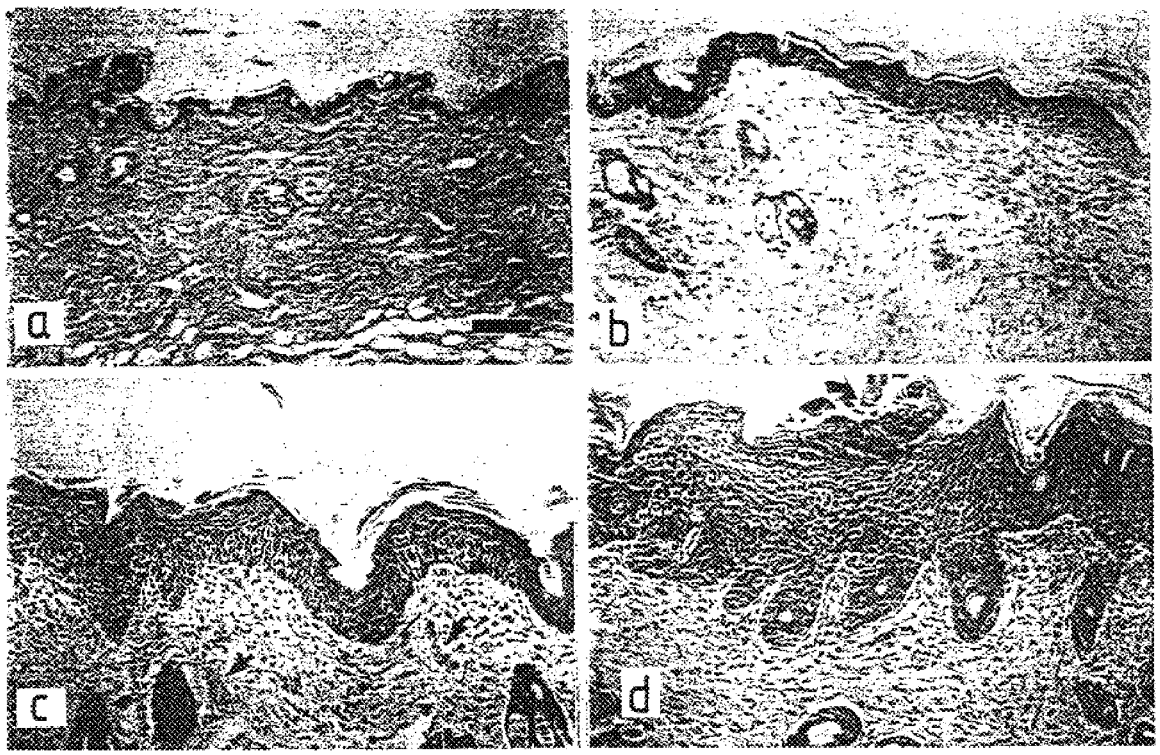

The epidermis of adult mice expressing $\beta_1$, $\alpha_2\beta_1$ or $\alpha_5\beta_1$ was examined histologically for evidence of abnormal proliferation and differentiation (FIG. 14). There were no clear differences between $\beta_1$, $\alpha_2\beta_1$ or $\alpha_5\beta_1$ mice. Abnormal histology was usually focal in the epidermis and underlying dermis of mildly affected animals, but covered extensive areas of more severely affected mice. All biopsies were matched for age, sex and body site and transgene-negative littermates were compared wherever possible. Skin from all trunk sites showed abnormal histology, but skin from tail, ear tips and cheek did not. Different trunk sites of a given animal could show varying severity of phenotype, but there was no correlation between site (for example back versus belly) and severity.

FIG. 14 shows haematoxylin and eosin stained sections of skin from the back of a normal mouse (FIG. 14a) and sections of transgenic mouse skin (FIGS. 14b–d). FIGS. 14b–d have been chosen to show the variation in severity of epidermal hyperproliferation and inflammation. In mildly affected animals (FIG. 14b), epidermal thickening was often observed adjacent to a relatively unaffected alea; in the dermis directly below the thickened epidermis an increased cellularity was apparent. In more severely affected animals (FIG. 14c), there was widespread thickening of the epidermis, reflecting both an increase in the number of viable cell layers (acanthosis) and cornified layers (hyperkeratosis). There was hyperplasia (increased thickness) of the epidermis and alternating regions of anucleate (orthokeratotic) and nucleated (parakeratotic) cornified cells. The granular layer was absent in regions of parakeratosis. In the most severe phenotype there were neutrophil-containing pustules within or beneath the cornified layers and large numbers of lymphocytes and polymorphs within the epidermis (FIG. 14d). Dermal involvement was widespread in the intermediate and severely affected mice and was characterised by infiltration of lymphocytes and neutrophils into the dermis, dermal mitoses and dilated capillaries (FIGS. 14c,d). TUNEL (TdT-mediated dUTP-biotin nick end labelling) showed that there were no major differences in the number of keratinocytes with apoptotic nuclei in normal, mildly or severely affected epidermis.

The histological appearance of skin from the $\beta_1$, $\alpha_2\beta_1$ and $\alpha_5\beta_1$ mice suggested that keratinocyte proliferation was increased and that terminal differentiation was perturbed. This was confirmed by staining for Ki-67, a nuclear protein expressed by proliferating cells and for the epidermal keratins K1 and K6.

Relatively few Ki-67-positive cells were seen in the dorsal epidermis of nontransgenic mice and all of the positive cells were in the basal layer (6.2±0.8% of basal cells were Ki67-positive; FIG. 15a). In mildly affected epidermis of transgenic mice the number of Ki-67-positive cells in the basal layer was increased (32.6±4.6%; FIG. 15b), while in the most severely affected epidermis the majority of basal (79±7.4%) and many suprabasal keratinocytes were Ki-67-positive (FIG. 14c). Increased Ki-67 labelling was also noted in the hair follicles (cf FIGS. 15a–c).

In normal and mildly affected epidermis K1 was expressed by all keratinocytes that had left the basal layer (FIGS. 14d,e) but in severely affected epidermis keratin 1 expression was patchy (FIG. 15f). In normal skin K6 expression was confined to the hair follicles (FIG. 15g), but in the transgenic mice K6 was expressed in hyperproliferative epidermis (FIGS. 15h,i). FIG. 15h shows the boundary between areas of normal and mildly hyperproliferative epidermis with strong K6 staining suprabasally in the affected region. FIG. 15i shows a severely affected area, where K6 staining of all the epidermal layers is apparent.

Characterisation of the Inflammatory Infiltrate in the Skin of Transgenic Mice

In order to investigate the nature of the inflammatory infiltrate in the affected mice, sections of dorsal skin were labelled with antibodies to the T-lymphocyte markers CD3 (T cell receptor, pan T-cell marker), CD4 and CD8, and to ICAM-1 (CD54), which is induced on the surface of keratinocytes by proinflammatory stimuli. Control mouse skin contained resident dendritic CD3-positive cells in the epidermis and hair follicles (most probably γδ T-cells), but no CD4, CD8 or ICAM-1 positive cells (FIGS. 16a,d,g,j).

In mildly hyperproliferative epidermis the number of CD3-positive dendritic cells in the epidermis (but not in the hair follicles) was reduced (FIG. 16b), while CD8-positive lymphocytes were present in the epidermis (FIG. 16h). CD4positive cells were present in the epidermis and dermis (FIG. 16e). Intense focal staining for ICAM-1 was observed in all layers of the epidermis and in the underlying dermis (FIG. 16k).

In the most severely affected mice, there were many more CD8-positive lymphocytes in the epidermis than found in mildly affected animals (compare FIGS. 16h,i) and the number of CD4-positive cells in the dermis was also increased (compare FIGS. 16e,f). There were numerous CD3-positive cells in the epidermis and dermis (FIG. 16c). ICAM-1 staining was less intense but more extensive in the severe lesions (FIG. 16l) than in mildly affected epidermis (FIG. 16k).

We have characterised the early events in the phenotype. The earliest event seems to be roughly five-fold increase in epidermal proliferation in transgenic skin which exhibits no other phenotype (see FIG. 15). This is judged by staining frozen sections of mouse skin with an antibody to Ki67, a marker of cell proliferation. Similar results were obtained by injecting BrdU into control and transgenic mice and staining with anti-BrdU antibody. In more severely affected animals, roughly 80% of the basal cells are proliferating, and there are numerous suprabasal mitoses as well. All of this indicates that integrins expressed suprabasally feedback to control the rate of epidermal proliferation in the basal layer, and this may well result in the ensuing immune response. Such abnormal proliferation has always been considered one of the hallmarks of psoriasis, andthought to be an early event.

Discussion

Adult transgenic mice expressing the $\beta_1$ transgene, alone or in combination with $\alpha_2$ or $\alpha_5$, had many features reminiscent of psoriasis, specifically psoriasis vulgaris. In humans and these mice the early changes include increased proliferation of basal keratinocytes, hyperkeratosis (ie increased number of cornified cells), increased dermal mitoses and capillary enlargement, and an influx of CD4-positive and CD8-positive T lymphocytes. More severe lesions are characterised by severe hyperplasia (thickening of the epidermis), regions of parakeratosis with loss of underlying granular cells, and large numbers of epidermal CD8-positive cells and of dermal CD4-positive cells. In the mice neutrophil containing pustules similar to the Munro microabscesses of psoriasis were commonly observed. As in psoriasis there was induction of ICAM-1 and an increase in Ki-67 labelling; keratin 6 was induced in the interfollicular epidermis and the level of keratin 1 was decreased. The only major feature of psoriasis not reproduced in the mice is elongation of the rete ridges, but since the dermo-epidermal junction in normal mice is flat this is hardly surprising.

Psoriasis is believed to have genetic and environmental components and this could explain the degree of penetrance of the phenotype in our mice.

EXAMPLE 2
Microinjection of Mouse Zygotes

A zygote is a one-cell stage embryo. It is preferred that the embryos are zygotes when they are injected, and divide once or twice to become blastocysts before implantation.

Six week-old female mice are induced to superovulate by injection of 5 international units of pregnant mares' serum, followed eighteen hours later by 2½ international units human chorionic gonadotropin, and placed immediately with males for mating. Approximately fourteen hours following mating, those females exhibiting vaginal plugs are sacrificed and their oviducts removed and placed in Krebs-Ringer bicarbonate buffered medium, containing bovine serum albumin and hyaluronidase at 1 mg/ml. Oviducts are opened with forceps and fertilized eggs and remaining follicle cells are expressed into a culture dish. After 1–2 minutes, eggs are removed and washed with culture medium previously equilibrated with 5% $CO_2$ in air at 37° C. Eggs containing pronuclei are identified under a dissecting microscope and placed in lots of twenty in a microdrop of equilibrated medium, which is then placed in a 100 mm culture dish and covered with mineral oil. Eggs are stored in the incubator in this manner until microinjected.

Microneedles having a tip diameter of about 1–2 cm are pulled from thin-walled glass tubing using a pipette puller. Holding pipettes (for holding eggs) having a tip diameter of 60–70 cm are similarly pulled from capillary tubing, and the ends fire polished using a microforge. The tips of the microneedles are allowed to fill with a suspension of plasmid DNA by capillary action. The holding pipettes and microneedle barrels are filled with an inert fluorocarbon (Fluorinert, 3M), and each microneedle and holding pipette is then secured to polyethylene tubing of appropriate diameter, which is in turn fitted to 1 ml Hamilton syringes secured in micromanipulators. Both microneedle and holding pipette apparatus are secured to the stage of a light microscope having a 1200× objective.

The culture dish containing the suspended zygotes is secured to the microscope stage in proximity to the microinjection apparatus, and a microneedle containing plasmid solution is moved close to the drop containing the zygotes. A zygote is then positioned on the holding pipette such that the male pronucleus is in focus, and the microneedle slowly inserted into the pronucleus. Sufficient plasmid suspension, (about 2 pl) is injected to approximately double the size of the pronucleus, and then the microneedle is slowly withdrawn. This procedure is repeated with the remaining fertilized eggs.

After an additional hour of incubation, surviving eggs are transferred to the oviducts of plugged pseudopregnant female mice as follows. Each foster female is anaesthetized with 6 mg/100 g sodium pentobarbital, and ovaries are located through a dorsal incision. The ovarian bursa is dissected from the supporting tissues with forceps, and the ostium of the oviduct visualised under the dissecting microscope. A pipette containing 10–20 microinjected embryos is inserted into the oviduct, and the wound closed. Approximately twenty days later, mice are examined for delivery of live offspring.

After weaning, tail tips or ear punches are taken from offspring and high molecular weight DNA isolated. The isolated DNA are then screened for the presence of heterologous DNA. On this basis, transgenic animals are identified and isolated.

EXAMPLE 3
Generation of Transgenic Pigs

The same DNA constructs as for the transgenic mice are microinjected into pig ova as set forth below in order to produce transgenic pigs.

Estrus is synchronized in sexually mature gilts (>7 months of age) by feeding an orally active progestogen (allyl trenbolone, AT: 15 mg/gilt/day) for 12 to 14 days. On the last day of AT feeding all gilts receive an intramuscular injection (IM) of prostaglandin $F_2$ (Lutalyse: 10 mg/injection) at 0800 and 1600. Twenty-four hours after the last day of AT consumption all donor gilts receive a single IM injection of pregnant mare serum gonadotropin (PMSG: 1500 RU). Human chorionic gonadotropin (HCG: 750 IU) is administered to all donors at 80 hours after PMSG.

Following AT withdrawal, donor and recipient gilts are checked twice daily for signs of estrus using a mature boar. Donors which exhibited estrus within 36 hours following HCG administration are bred at 12 and 24 hours after the onset of estrus using artificial and natural (respectively) insemination.

Between 59 and 66 hours after the administration of HCG, one- and two-cell ova are surgically recovered from bred donors using the following procedure. General anaesthesia is induced by administering 0.5 mg of acepromazine/kg of bodyweight and 1.3 mg ketamine/kg of bodyweight via a peripheral ear vein. Following anaesthetization, the reproductive tract is exteriorized following a mid-ventral laparotomy. A drawn glass cannula (OD 5 mm, length 8 cm) is inserted into the ostium of the oviduct and anchored to the infindibulum using a single silk (2–0) suture. Ova are flushed in retrograde fashion by inserting a 20 g needle into the lumen of the oviduct 2 cm anterior to the uterotubal junction. Sterile Dulbecco's phosphate buffered saline (PBS) supplemented with 0.4% bovine serum albumin (BSA) is infused into the oviduct and flushed toward the glass cannula. The medium is collected into sterile 17×100 mm polystyrene tubes. Flushings are transferred to 10×60 mm petri dishes and searched at lower power (50×) using a Wild M3 stereomicroscope. All one- and two-cell ova are washed twice in Brinster's Modified Ova Culture-3 medium (BMOC-3) supplemented with 1.5% BSA and transferred to 50 $\mu$l drops of BMOC-3 medium under oil. Ova are stored at 38° C. under a 90% $N_2$, 5% $O_2$, 5% $CO_2$ atmosphere until microinjection is performed.

One- and two-cell ova are placed in an Eppendorf tube (15 ova per tube) containing 1 ml HEPES Medium supplemented with 1.5% BSA and vicentrifuged for six minutes at 14000×g in order to visualize pronuclei in one-cell and nuclei in two-cell ova. Ova are then transferred to a 5–10 $\mu$l drop of HEPES medium under oil on a depression slide. Microinjection is performed using a Laborlux microscope with Nomarski optics and two Leitz micromanipulators. 10–1700 copies of construct DNA (1 ng/$\mu$l of Tris-EDTA buffer) are injected into one pronuclei in one-cell ova or both nuclei in two-cell ova.

Microinjected ova are returned to microdrops of BMOC-3 medium under oil and maintained at 38° C. under 1 90% $N_2$, 5% $CO_2$, 5% $O_2$ atmosphere prior to their transfer to suitable recipients. Ova are transferred within ten hours of recovery.

Only recipients which exhibited estrus on the same day or 24 hours later than the donors are utilized for embryo transfer. Recipients are anaesthetized as described earlier. Following exteriorization of one oviduct, at least 30 injected one- and/or two-cell ova and 4–6 control ova are transferred in the following manner. The tubing from a 21 g×¾ butterfly infusion set is connected to a 1 ml syringe. The ova and one to two mls of BMOC-3 medium are aspirated into the tubing. The tubing is then fed through the ostium of the oviduct until the tip reached the lower third or isthmus of the oviduct. The ova are subsequently expelled as the tubing was slowly withdrawn.

The exposed portion of the reproductive tract is bathed in a sterile 10% glycerol-0.9% saline solution and returned to the body cavity. The connective tissue encompassing the linea alba, the fat and the skin are sutured as three separate layers. An uninterrupted Halstead stitch is used to close the linea alba. The fat and skin are closed using a simple continuous and mattress stitch, respectively. A topical antibacterial agent (Furazolidone) was then administered to the incision area.

Recipients are penned in groups of four and fed 1.8 kg of a standard 16% crude protein corn-soybean pelleted ration. Beginning on day 18 (day 0 =onset of estrus), all recipients are checked daily for signs of estrus using a mature board. On day 35, pregnancy detection was performed using ultrasound. On day 107 of gestation recipients are transferred to the farrowing suite. In order to ensure attendance at farrowing time, farrowing is induced by the administration of prostaglandin $F_2$ (10 mg/injection) at 0800 and 1400 hours on day 112 of gestation. Recipients farrow within 34 hours following PGF2a administration.

Twenty-four hours after birth, all piglets are processed, ie ears were notched, needle teeth clipped, 1 ml of iron dextran is administered, etc. A tail biopsy and blood were also obtained from each pig. The transgenic nature of the pig is confirmed by DNA analysis of the transgene using PCR.

What is claimed is:

1. A transgenic mouse whose genome comprises a transgene, said transgene comprising a gene encoding at least one human integrin $\alpha$ subunit selected from the group consisting of $\alpha_6$ and $\alpha_v$ operatively linked to a human involucrin promoter, wherein said transgene is expressed in the suprabasal cells of the epidermis, and wherein said transgenic mouse develops a symptom of psoriasis comprising epidermal hyperproliferation as a result of expression of said transgene.

2. A transgenic mouse whose genome comprises a transgene, said transgene comprising a gene encoding human integrin $\beta1$ subunit operatively linked to a human involucrin promoter, wherein said transgene is expressed in the suprabasal cells of the epidermis, and wherein said transgenic mouse develops a symptom of psoriasis comprising epidermal hyperproliferation as a result of expression of said transgene.

3. A transgenic mouse whose genome comprises a combination of transgenes, said combination of transgenes encoding at least one human integrin subunit combination selected from the group consisting of $\alpha_2\beta_1$, $\alpha_3\beta_1$, $\alpha_5\beta_1$, and $\alpha_6\beta_1$, each transgene being operatively linked to a human involucrin promoter, wherein said transgenes are expressed in the suprabasal cells of the epidermis, and wherein said transeenic mouse develops a symptom of psoriasis comprising epidermal hyperproliferation as a result of expression of said transgenes.

4. A method of making a transgenic mouse which develops a symptom of psoriasis comprising epidermal hyperproliferation as a result of expression of a transgene encoding a human integrin subunit selected from the group consisting of $\beta_1$, $\alpha_6$ and $\alpha_v$ in a suprabasal cell of the epidermis, said method comprising the steps of (a) introducing into a mouse embryo a nucleic acid construct comprising said transgene operatively linked to a human involucrin promoter which directs expression of said transgene in the suprabasal cells of the epidermis;

(b) introducing the embryo from step (a) into a pseudopregnant female mouse;

(c) sustaining the female, in step (b) until the embryo has developed to be independent of said female; and (d) selecting from the progeny of said female a transgenic mouse which develops said symptoms of psoriasis.

5. A method of making a transgenic mouse which develops a symptom of psoriasis comprising epidermal hyperproliferation as a result of expression of a combination of transgenes encoding at least one human integrin subunit combination selected from the group consisting of $\alpha_2\beta_1$, $\alpha_3\beta_1$, $\alpha_5\beta_1$ and $\alpha_6\beta_1$ in a suprabasal cell of the epidermis, said method comprising the steps of (a) mating a mouse which expresses at least one human integrin subunit selected from the group consisting of $\alpha_2$, $\alpha_3$, $\alpha_5$ and $\alpha_6$, in a suprabasal cell of the epidermis due to the presence of a first transgene encoding said subunit operably linked to a human involucrin promoter, with a mouse which expresses the $\beta_1$-integrin subunit in a suprabasal cell of the epidermis due to the presence of a second transgene operably linked to a human involucrin promoter and (b) selecting an offspring of said mating which expresses said combination in a suprabasal cell of the epidermis.

6. A suprabasal cell derived from a transgenic mouse according to claim 1.

7. A method of selecting a compound which potentially reduces or eliminates psoriasis comprising (a) administering said compound to a transgenic mouse according to claim 1 and (b) determining whether the compound reduces or eliminates psoriasis.

8. The method according to claim 7 wherein the compound is administered topically.

9. A suprabasal cell derived from a transgenic mouse according to claim 2.

10. A suprabasal cell derived from a transgenic mouse according to claim 3.

11. A method of selecting a compound which potentially reduces or eliminates psoriasis comprising (a) administering said compound to a transgenic mouse according to claim 2 and (b) determining whether the compound reduces or eliminates psoriasis.

12. A method of selecting a compound which potentially reduces or eliminates psoriasis comprising (a) administering said compound to a transgenic mouse according to claim 3 and (b) determining whether the compound reduces or eliminates psoriasis.

13. The method according to claim 11 wherein the compound is administered topically.

14. The method according to claim 12 wherein the compound is administered topically.

* * * * *